United States Patent
Shimuta

(10) Patent No.: US 12,158,378 B2
(45) Date of Patent: Dec. 3, 2024

(54) STICKING-TYPE CORE BODY THERMOMETER

(71) Applicant: Murata Manufacturing Co., Ltd., Nagaokakyo (JP)

(72) Inventor: Toru Shimuta, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 830 days.

(21) Appl. No.: 17/199,558

(22) Filed: Mar. 12, 2021

(65) Prior Publication Data

US 2021/0199514 A1 Jul. 1, 2021

Related U.S. Application Data

(63) Continuation of application No. PCT/JP2019/044144, filed on Nov. 11, 2019.

(30) Foreign Application Priority Data

Nov. 13, 2018 (JP) .................................. 2018-212780

(51) Int. Cl.
*G01K 13/20* (2021.01)
*A61B 5/01* (2006.01)
(Continued)

(52) U.S. Cl.
CPC ................. *G01K 13/20* (2021.01); *A61B 5/01* (2013.01); *G01K 3/10* (2013.01); *G01K 7/427* (2013.01); *A61B 2562/0271* (2013.01)

(58) Field of Classification Search
CPC .......... G01K 13/20; G01K 3/10; G01K 7/427; G01K 1/143; G01K 7/42; G01K 7/00;
(Continued)

(56) References Cited

U.S. PATENT DOCUMENTS 4,231,085 A * 10/1980 Bazlen .................... G06F 9/226
 712/213
2011/0224936 A1* 9/2011 Shimizu ................. G01K 13/20
 702/99

(Continued)

FOREIGN PATENT DOCUMENTS

JP 2009222543 A 10/2009
JP 2012154859 A 8/2012
(Continued)

OTHER PUBLICATIONS

JP-2018021833-A English Translation (Year: 2018).*
(Continued)

*Primary Examiner* — Daniel L Cerioni
*Assistant Examiner* — Andrew E Hoffpauir
(74) *Attorney, Agent, or Firm* — ArentFox Schiff LLP

(57) ABSTRACT

A calculation processing unit of a sticking-type core body thermometer includes a correction value acquisition unit and a core body temperature acquisition unit. The correction value acquisition unit obtains a first correction value used to correct a first temperature, in accordance with a first differential value between a reference temperature set in advance according to a maximum limit body temperature and the first temperature on a sticking surface side of a first thermal resistor, and obtains a second correction value that is a correction value used to correct the first temperature, in accordance with a second differential value between the first temperature and a second temperature on a back surface side of the first thermal resistor. The core body temperature acquisition unit obtains a core body temperature by correcting the first temperature by using the first correction value and the second correction value.

18 Claims, 15 Drawing Sheets

(51) Int. Cl.
*G01K 3/10* (2006.01)
*G01K 7/42* (2006.01)

(58) Field of Classification Search
CPC .............. A61B 5/01; A61B 2562/0271; A61B 2560/0247; A61B 5/6832
See application file for complete search history.

(56) References Cited

U.S. PATENT DOCUMENTS

| | | | |
|---|---|---|---|
| 2012/0238901 A1* | 9/2012 | Augustine | A61B 5/01 600/549 |
| 2017/0296114 A1* | 10/2017 | Ghaffari | A61B 5/4266 |
| 2018/0136051 A1* | 5/2018 | Ishii | G01K 1/20 |
| 2018/0184908 A1* | 7/2018 | Meyerson | A61B 5/6833 |

FOREIGN PATENT DOCUMENTS

| | | | | |
|---|---|---|---|---|
| JP | 2016109518 A | | 6/2016 | |
| JP | 2017217224 A | | 12/2017 | |
| JP | 2018013395 A | | 1/2018 | |
| JP | 2018021833 A | * | 2/2018 | |
| KR | 2015137395 A | * | 12/2015 | .............. G08B 21/00 |
| WO | WO-2017183709 A1 | * | 10/2017 | .............. G01K 13/20 |

OTHER PUBLICATIONS

WO-2017183709-A1 English Translation (Year: 2017).*
KR-2015137395-A English Translation (Year: 2015).*
Written Opinion of the International Search Authority issued for PCT/JP2019/044144, date of mailing Jan. 28, 2020.
International Search Report issued for PCT/JP2019/044144, date of mailing Jan. 28, 2020.

* cited by examiner

STICKING-TYPE CORE BODY THERMOMETER

CROSS-REFERENCE TO RELATED APPLICATIONS

The present application is a continuation of International Application No. PCT/JP2019/044144, filed Nov. 11, 2019, which claims priority to Japanese Application No. 2018-212780, filed on Nov. 13, 2018, the entire contents of each of which are incorporated herein by reference.

TECHNICAL FIELD

The present disclosure relates to a sticking-type core body thermometer that is stuck to a living body to measure a core body temperature.

BACKGROUND

Conventionally, thermometers are placed on a body surface to acquire body temperature data through continuous measurements. In one approach as described in Japanese Unexamined Patent Application Publication No. 2012-154859 ("Patent Document 1"), a non-heating-type core body thermometer is placed on a body surface of a subject to measure a core body temperature of the subject. The core body thermometer includes two thermal resistors. In each resistor, a first temperature sensor is disposed on one-side surface that comes in contact with a body surface and a second temperature sensor disposed on an other-side surface opposite from the one side surface. The core body thermometer further includes an equalizing member configured to cover only the other-side surface of each of the first and second thermal resistors, a thermal insulation member disposed to surround a side surface of each of the first and second thermal resistors, and a protective member of which a peripheral portion is fixed to the other-side surface of the thermal insulation member and a center portion is disposed with a predetermined space from the equalizing member.

To remove the influence of a disturbance received by the equalizing member, that is, a rapid temperature change in the environment (a side across from a side contacting with a body surface), the core body thermometer improves measurement accuracy with a configuration to not block heat flow from an inside to an outside and to interrupt a disturbance from the outside to the equalizing member.

However, for the above-described core body thermometer in Patent Document 1, causes of errors other than an outside rapid temperature change (disturbance) are not considered. For example, the amount of heat that transfers fluctuates due to variations in blood flow in skin; however, such a heat transfer or the like in skin is not considered for the above-described core body thermometer. When sweating occurs, a body surface temperature decreases due to heat of evaporation at the time when sweat evaporates; however, sweat is hard to evaporate in an area where the core body thermometer is stuck as compared to the surrounding area, so a decrease in body surface temperature is small. For this reason, the temperature is higher than the surrounding area, and heat transfers to the surrounding area due to heat conduction of skin and blood flow; however, such a heat transfer in skin is also not considered for the above-described core body thermometer. Therefore, an estimated core body temperature may deviate from an actual value.

SUMMARY

The present disclosure is contemplated to solve the above problem, and it is an object of the present disclosure to provide a sticking-type core body thermometer that is stuck to a living body to measure a core body temperature and that further improves core body temperature measurement accuracy.

A sticking-type core body thermometer according to the present disclosure is a sticking-type core body thermometer that is stuck to a living body to measure a body temperature and that includes: a thermal resistor having a predetermined thermal resistance; a first temperature detection unit that is disposed on one-surface side of the thermal resistor and that detects a first temperature of a sticking surface side; a correction value acquisition unit that obtains a first correction value that is a correction value used to correct the first temperature, in accordance with a first differential value that is a differential value between the first temperature and a reference temperature set to a temperature higher than the first temperature; and a core body temperature acquisition unit that obtains a core body temperature by correcting the first temperature by using the first correction value.

With the sticking-type core body thermometer according to the present disclosure, a first temperature on the sticking surface side of the thermal resistor is detected, a first correction value used to correct the first temperature is obtained in accordance with a first differential value between the first temperature and a reference temperature set in advance to a temperature higher than the first temperature, and a core body temperature is obtained by correcting the first temperature by using the first correction value. By using a first differential value between a first temperature on a sticking surface side (body surface side) and a reference temperature set to a temperature higher than the first temperature as a parameter, when, for example, the first temperature (body surface temperature) increases with an increase in heat radiation from the body surface and, as a result, the body surface temperature approaches a core body temperature, the first differential value reduces. In this case, measurement accuracy is improved by reducing the first correction value. On the other hand, when the first temperature (body surface temperature) decreases with a reduction in heat radiation from the body surface and, as a result, the body surface temperature deviates from the core body temperature, the first differential value increases. In this case, measurement accuracy is improved by increasing the first correction value. In this way, physiological response associated with thermoregulation by sweat and blood flow can be considered, so consistency with an actual core body temperature is enhanced. Thus, a core body temperature is highly accurately obtained with relatively simple calculation.

According to the present disclosure, in a sticking-type core body thermometer that is stuck to a living body to measure a core body temperature, core body temperature measurement accuracy is further improved.

The above simplified summary of example aspects serves to provide a basic understanding of the present disclosure. This summary is not an extensive overview of all contemplated aspects, and is intended to neither identify key or critical elements of all aspects nor delineate the scope of any or all aspects of the present disclosure. Its sole purpose is to present one or more aspects in a simplified form as a prelude to the more detailed description of the disclosure that follows. To the accomplishment of the foregoing, the one or more aspects of the present disclosure include the features described and exemplarily pointed out in the claims.

BRIEF DESCRIPTION OF THE DRAWINGS

The accompanying drawings, which are incorporated into and constitute a part of this specification, illustrate one or more example aspects of the present disclosure and, together with the detailed description, serve to explain their principles and implementations.

DETAILED DESCRIPTION

Figure 1:
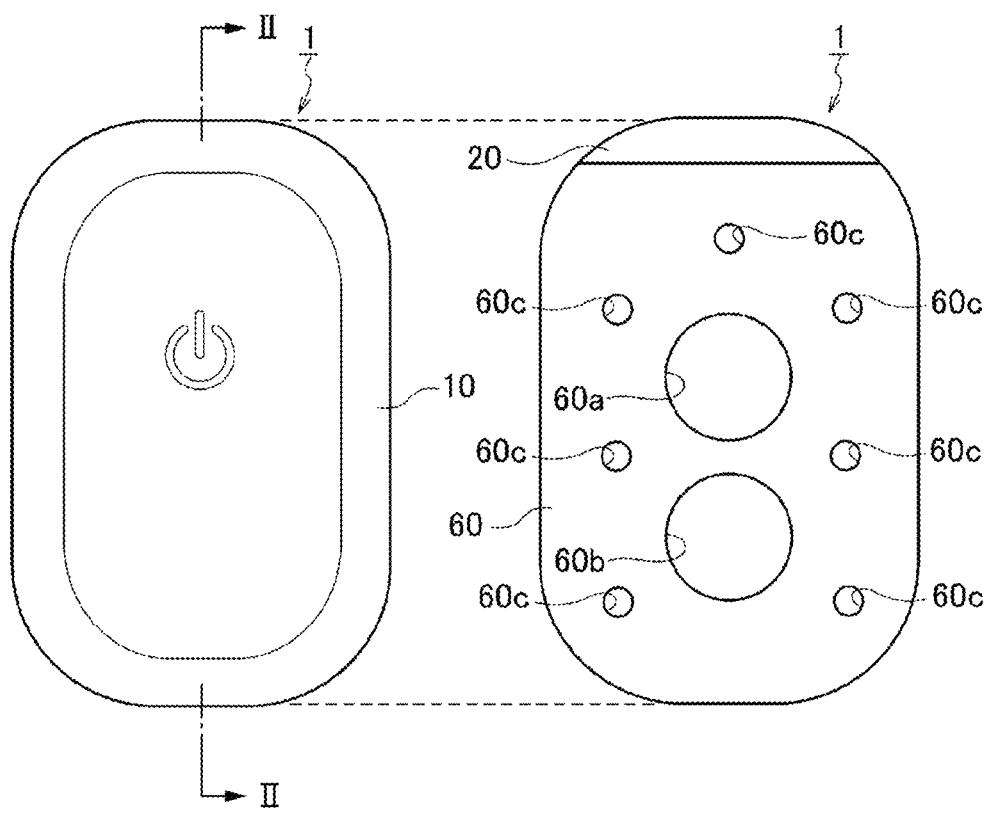
FIG. 1 shows a plan view and a bottom view showing the appearance of a sticking-type core body thermometer according to a first embodiment.

Hereinafter, preferred embodiments of the present disclosure will be described in detail with reference to the drawings. In the drawings, like reference signs are assigned to the same or corresponding portions. In the drawings, like reference signs denote the same components, and the description is omitted.

Figure 2:
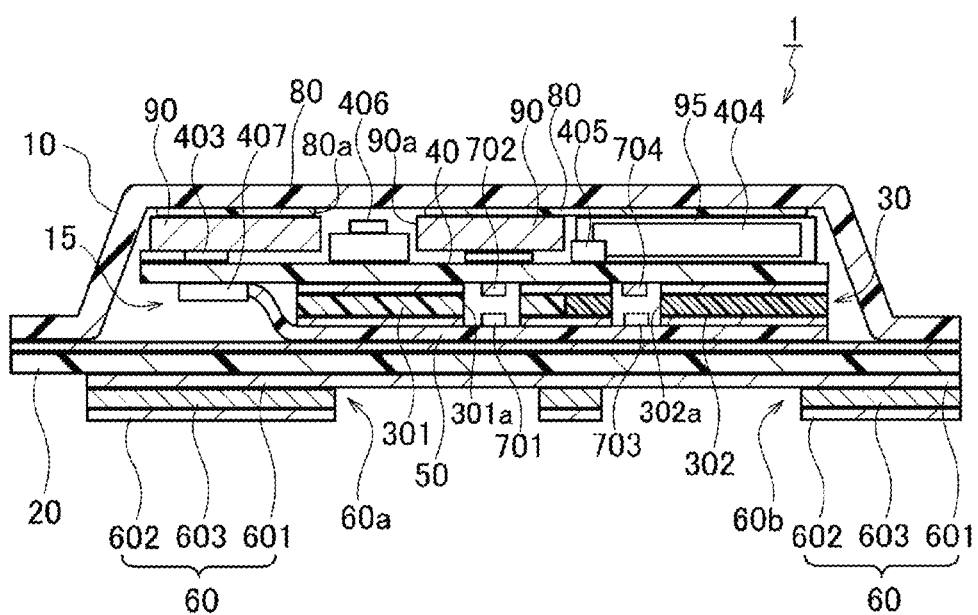
FIG. 2 is a cross-sectional view showing the configuration of the sticking-type core body thermometer according to the first embodiment.
Figure 3:
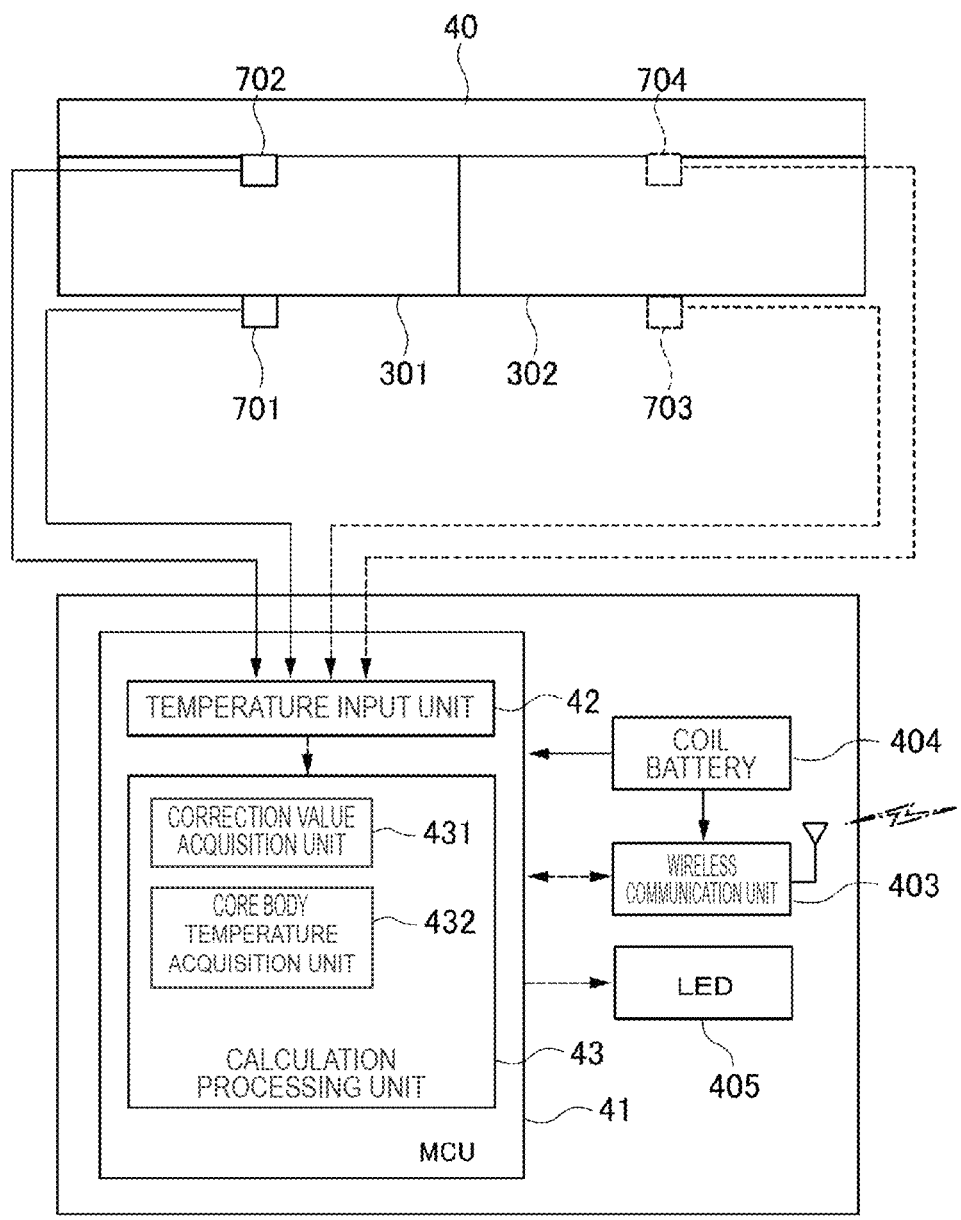
FIG. 3 is a block diagram showing the functional configuration of a processing unit that is a component of the sticking-type core body thermometer according to the first embodiment.

First, the configuration of a sticking-type core body thermometer (hereinafter, which may be simply referred to as core body thermometer, deep body thermometer, or thermometer) 1 according to the embodiment will be described with reference to FIG. 1 to FIG. 3. FIG. 1 shows a plan view and a bottom view showing the appearance of the sticking-type core body thermometer 1. FIG. 2 is a cross-sectional view showing the configuration of the sticking-type core body thermometer 1 (cross-sectional view taken along the line II-II in FIG. 1). FIG. 3 is a block diagram showing the functional configuration of a processing unit 41 that is a component of the sticking-type core body thermometer 1.

The core body thermometer 1 is a non-heating-type core body thermometer that obtains a heat flow from a deep part of a user (subject) to acquire a core body temperature in accordance with temperatures respectively detected by a first temperature sensor 701 (which corresponds to a first temperature detection unit or first temperature detection detector) and a second temperature sensor 702 (which corresponds to a second temperature detection unit or first temperature detection detector) and/or temperatures respectively detected by a third temperature sensor 703 and a fourth temperature sensor 704. The core body thermometer 1 is a sticking-type (patch-type) core body thermometer that is stuck to a body surface of a user (subject) to acquire body temperature data by continuously measuring a body temperature.

As shown, the core body thermometer 1 mainly includes an upper exterior body 10, a lower exterior body 20, a body temperature measurement unit 15, a lining member 80, a shock-absorbing member 90, and a sticking member 60. The body temperature measurement unit 15 mainly includes a thermal resistor layer 30, a wiring substrate 40, and a flexible substrate 50. The second temperature sensor 702 and the fourth temperature sensor 704 are mounted on the wiring substrate 40. The first temperature sensor 701 and the third temperature sensor 703 are mounted on the flexible substrate 50.

The upper exterior body 10 is made of, for example, a closed-cell or semi-closed-cell foamed material having waterproof and heat retaining properties. The upper exterior body 10 is preferably made of a foamed material having a low thermal conductivity to prevent a local change in the temperature of the body temperature measurement unit 15 due to a steep variation (change) in outside air temperature. For example, polyurethane, polystyrene, polyolefin, or the like is suitably used as the material. For example, vacuum forming is suitably used as a method of machining the upper exterior body 10. The upper exterior body 10 has a substantially hat shape in cross section so that the body temperature measurement unit 15 (the thermal resistor layer 30, the wiring substrate 40, the flexible substrate 50, and the like) can be accommodated. Therefore, the side surface of the thermal resistor layer 30 is covered with a foamed material, and exposure of the side surface of the thermal resistor layer 30 to outside air is prevented.

The lower exterior body 20 is made from, for example, a non-foamed resin film having a waterproof property (low moisture permeability) and a higher thermal conductivity than the upper exterior body 10. Examples of the material include polypropylene, polyethylene, polyester, and polyimide. Particularly, polyethylene terephthalate is suitably used as the material. The lower exterior body 20 is formed in a planar shape (flat) so that the flexible substrate 50 on which the first temperature sensor 701 and the third temperature sensor 703 are mounted (the body temperature measurement unit 15) can be fixed in close contact with the lower exterior body 20. When there is a gap between the body temperature measurement unit 15 and the lower exterior body 20, a thermal resistance varies and influences heat flux, so the body temperature measurement unit 15 and the lower exterior body 20 are desirably fixed in close contact with each other by a sticking method with double-faced adhesive tape, a fixing method with adhesive, or the like. The upper exterior body 10 and the lower exterior body 20 are formed to have the same or substantially the same sizes (outside dimensions) and are formed to have a size of, for example, about 40 mm to about 100 mm long and about 20 mm to about 60 mm wide.

A peripheral portion of the upper exterior body 10 formed in a substantially hat shape in cross section and a peripheral portion of the lower exterior body 20 formed in a planar shape are, for example, brought into close contact with each other by sticking with double-faced adhesive tape, fixing with adhesive, heat sealing, or the like. To implement waterproof performance, it is desirable that a portion where the upper exterior body 10 and the lower exterior body 20 are fixed in close contact with each other be flat and less prone to wrinkling. In other words, it is desirable that the outer peripheral portion of the lower exterior body 20 be flat, the outer peripheral portion of the opposed upper exterior body 10 be also flat, and those be stuck to each other to be fixed in close contact with each other. With this configuration, a force uniformly acts on a close contact fixing portion, so such an inconvenience that adversely influences waterproof performance, such as wrinkling, is less likely to occur.

As shown in FIG. 2, the body temperature measurement unit 15 is made by laminating the flexible substrate 50, the thermal resistor layer 30, and the wiring substrate 40 in this order from the lower exterior body 20 side.

The thermal resistor layer 30 includes two thermal resistors having different thermal resistance values, that is, a first thermal resistor 301 and a second thermal resistor 302, to form two heat fluxes. A material having a lower thermal conductivity (higher thermal resistance value) than the second thermal resistor 302, for example, foamed plastics (foamed material), such as polyurethane, polystyrene, and polyolefin, is suitably used as the first thermal resistor 301. Non-foamed plastics, rubber, or the like may also be used. A material having a higher thermal conductivity (lower thermal resistance value) than the first thermal resistor 301, for example, plastics, such as polypropylene, polyethylene, acrylic, polycarbonate, and epoxy resin, is suitably used as the second thermal resistor 302. Here, the thermal conductivity of a metal, such as copper and aluminum, is higher than or equal to 100 [W/m/K]; whereas the thermal conductivity of plastics, such as polypropylene, polyethylene, acrylic, polycarbonate, and epoxy resin, is about 0.1 to 0.5 [W/m/K] and lower by about three orders of magnitude. The thermal conductivity of foamed plastics is further lower by about an order of magnitude. The thermal conductivity of air is further lower and is 0.024 [W/m/K]. The first thermal resistor 301 and the second thermal resistor 302 are formed to have substantially the same thickness in order to reduce cost by enabling the first thermal resistor 301 and the second thermal resistor 302 to be stacked with the wiring substrate 40 and the flexible substrate 50.

The first thermal resistor 301 that is a component of the thermal resistor layer 30 has a first through-hole 301a extending through in a thickness direction. Similarly, the second thermal resistor 302 that is a component of the thermal resistor layer 30 has a second through-hole 302a extending through in the thickness direction. When the first through-hole 301a is viewed in plan, the first through-hole 301a is formed such that the first temperature sensor 701 and the second temperature sensor 702 are accommodated inside. In other words, the pair of first temperature sensor 701 and second temperature sensor 702 is disposed along the thickness direction of the first thermal resistor 301 within (inside) the first through-hole 301a. Similarly, when the second through-hole 302a is viewed in plan, the second through-hole 302a is formed such that the third temperature sensor 703 and the fourth temperature sensor 704 are accommodated inside. In other words, the pair of third temperature sensor 703 and fourth temperature sensor 704 is disposed along the thickness direction of the second thermal resistor 302 within (inside) the second through-hole 302a.

For example, a thermistor, a resistance thermometer sensor, or the like is suitably used as each of the first temperature sensor 701 to the fourth temperature sensor 704 (hereinafter, which may be collectively referred to as temperature sensors 70). Each temperature sensor 70 desirably has a thermal capacity as small as possible from the viewpoint of enhancing response. Thus, for example, a chip thermistor is suitably used as each temperature sensor 70. Each of the first temperature sensor 701 to the fourth temperature sensor 704 is electrically connected to the processing unit 41 (processing circuit) (described later) via a printed circuit, and the processing unit 41 reads an electrical signal (voltage value) corresponding to a temperature.

Incidentally, to reduce the size of the heat flow core body thermometer 1, it is important to reduce the size of the thermal resistor layer 30 (the first thermal resistor 301 and the second thermal resistor 302); however, when the size of the thermal resistor layer 30 (the first thermal resistor 301 and the second thermal resistor 302) is reduced, a difference between the output values of the paired temperature sensors 70 reduces, so there are concerns that a measurement error increases. Here, each temperature sensor 70 (chip thermistor) has a substantially rectangular parallelepiped shape and has a thickness, so the thickness cannot be ignored when the thermal resistor layer 30 (the first thermal resistor 301 and the second thermal resistor 302) becomes thinner. When the temperature sensor 70 is in contact with the side surface of the thermal resistor layer 30 (the first thermal resistor 301 and the second thermal resistor 302), heat is transferred from the contact portion, so there are concerns that the temperature (detected value) of the temperature sensor 70 becomes a temperature (value) that deviates from the surface temperature of the thermal resistor layer 30 (the first thermal resistor 301 and the second thermal resistor 302). Therefore (to reduce the influence), the through-holes 301a, 302a are formed in the thermal resistor layer 30 (the first thermal resistor 301 and the second thermal resistor 302) around the temperature sensors 70 to provide such a structure that the temperature sensors 70 are not in contact with the side surface of the thermal resistor layer 30 (the first thermal resistor 301 and the second thermal resistor 302).

The wiring substrate 40 is, for example, a rigid substrate like a glass epoxy substrate. The processing unit 41 (processing circuit) is implemented on or in the wiring substrate 40. The processing unit 41 (processing circuit) acquires core body temperature data by processing output signals of the first temperature sensor 701 to the fourth temperature sensor 704. A wireless communication unit 403 and a coin battery 404 are mounted on the wiring substrate 40. The wireless communication unit 403 transmits (outputs) acquired core body temperature data. The coin battery 404 supplies electric power to the processing unit 41 and the wireless communication unit 403. The processing unit 41 mainly includes a temperature input unit 42 (temperature input circuit) and a calculation processing unit 43 (calculation processing circuit). The temperature input unit 42 is configured to include, for example, an amplifier (for example, an operational amplifier), an analog/digital converter (A/D converter), and the like to read detection signals (output voltages) of the temperature sensors 70. The temperature input unit 42 amplifies an analog signal output from each temperature sensor 70, converts the analog signal to a digital signal, and outputs the digital signal to the calculation processing unit 43.

The calculation processing unit 43 is made up of, for example, an MCU (micro control unit), EEPROM, RAM, and the like. The calculation processing unit 43 calculates a core body temperature from the read temperature data. The details will be described later.

The second temperature sensor 702 and the fourth temperature sensor 704 are mounted on the bottom surface of the wiring substrate 40. The second temperature sensor 702 acquires the temperature of the top surface (outside air side) of the first thermal resistor 301. The fourth temperature sensor 704 detects the temperature of the top surface (outside air side) of the second thermal resistor 302. More specifically, a pair of heat equalizing patterns that equalize a surrounding temperature distribution is formed on the bottom surface of the wiring substrate 40, one of electrodes of the second temperature sensor 702 is connected to one of the heat equalizing patterns, and one of electrodes of the fourth temperature sensor 704 is connected to the other one of the heat equalizing patterns. The pair of heat equalizing patterns is made of, for example, a material having a high thermal conductivity, such as a metal film.

To prevent a change in only the temperature of part of the wiring substrate 40 due to the influence of outside air temperature or the like, it is desirable that an equalizing member (metal film) that has a high thermal conductivity and that thermally equalizes the influence of a temperature distribution of outside air temperature be provided on the back surface side (outside air side) of a wiring layer on which the second temperature sensor 702 and the fourth temperature sensor 704 are mounted. A metal foil, a thin metal sheet, or the like may be used as the equalizing member, and, as in the case of the wiring layer formed on or in the wiring substrate 40, it is desirable that the equalizing member be formed as a wiring pattern (solid pattern) of an inner layer of the wiring substrate 40 (multilayer rigid substrate). In this case, the wiring pattern of the inner layer, used as the equalizing member, may be a ground pattern, and it is desirable that the wiring pattern be an independent pattern not connected to the electrical circuit and through which no current flows.

The wireless communication unit 403 transmits acquired core body temperature data or the like to an external management device and management system or a mobile terminal (for example, a smartphone or the like) of a manager or supervisor. Here, the wireless communication unit 403 transmits core body temperature data to the external management device and management system by using, for example, Bluetooth (registered trademark) or the like. On the other hand, the wireless communication unit 403 may receive, for example, outside air temperature data or the like from the external management device and management system or an information terminal.

The low-profile coin battery (battery) 404 supplies electric power to the above-described processing unit 41, wireless communication unit 403, and the like. The coin battery 404 is accommodated in a battery holder 95 mounted on (attached to) the wiring substrate 40. The battery holder 95 is disposed between the wiring substrate 40 and the lining member 80. In other words, the battery holder 95 also serves as a spacer member that supports the lining member 80. To reduce the plane area (sticking area) of the body temperature measurement unit 15 (core body thermometer 1), and also to prevent the influence of heat generation resulting from a change in outside air temperature or the operation of the wireless communication unit 403, the wireless communication unit 403 and the coin battery 404 (battery holder 95) are disposed across the wiring substrate 40 from the temperature sensors 70 (top surface side).

A power switch 406 is mounted on the top surface (main surface) of the wiring substrate 40. The power switch 406 receives user's on/off operation of the power via the upper exterior body 10. The wiring substrate 40 is accommodated in an enclosed space defined by the upper exterior body 10 and the lower exterior body 20 such that the power switch 406 faces the rear surface (back surface) of the upper exterior body 10. For example, a push button switch, a rocker switch, or the like is suitably used as the power switch 406. In the case of a push button switch, it is desirable that the push button switch be of an alternate action type that retains an on state even when a fingertip is released. A surface mount-type switch is desirable as the power switch 406; however, a reed-type switch may also be used.

To prevent erroneous (accidental) pushing down of the power switch 406 to turn on or off the power, and also to make the power switch 406 not push up the upper exterior body 10, the power switch 406 is disposed so as not to be in contact with the upper exterior body 10. More specifically, a clearance between the button top surface (top surface) of the power switch 406 and the rear surface (back surface) of the upper exterior body 10 is, for example, desirably set within a range of 0 mm to 4 mm and more desirably set within a range of 0.5 mm to 1.5 mm. The stroke of the power switch 406 is, for example, desirably set within a range of 0.1 mm to 1 mm and more desirably set within a range of 0.1 mm to 0.3 mm.

An LED 405 is mounted on the top surface of the wiring substrate 40. The LED 405 lights up or blinks in accordance with user's operation or the status of measurement of core body temperature (for example, an on/off state of the power switch 406, measurement start/stop, attachment/detachment state, and the like). For example, a VCSEL or the like may be used instead of the LED. In addition, an FPC connector 407 for electrically connecting the flexible substrate 50 is attached to the bottom surface side of the wiring substrate 40.

The flexible substrate 50 is made of, for example, polyimide, polyester, or the like and has flexibility. The first temperature sensor 701 and the third temperature sensor 703 are mounted on the flexible substrate 50. The first temperature sensor 701 acquires the skin-side temperature of the first thermal resistor 301. The third temperature sensor 703 acquires the skin-side temperature of the second thermal resistor 302. More specifically, a pair of heat equalizing patterns is formed on the flexible substrate 50 to equalize the surrounding temperature distribution, one of terminals of the first temperature sensor 701 is connected to one of the heat equalizing patterns, and one of terminals of the third temperature sensor 703 is connected to the other one of the heat equalizing patterns. The pair of heat equalizing patterns is made of, for example, a material having a high thermal conductivity, such as a metal film. Each of the first temperature sensor 701 and the third temperature sensor 703 is connected to the wiring substrate 40 (processing unit 41) via the wiring pattern and the above-described FPC connector 407. The processing unit 41 (temperature input unit 42) reads an electrical signal (voltage value) corresponding to a temperature. As described above, the lower exterior body 20, the flexible substrate 50, the thermal resistor layer 30, and the wiring substrate 40 form heat fluxes, so these components are, for example, fixed in close contact with each other by double-faced adhesive tape such that no gap is formed therebetween.

The lining member 80 is disposed between the rear surface (back surface) of the upper exterior body 10, that is, the upper exterior body 10, and both the shock-absorbing member 90 and the battery holder (spacer member) 95. The lining member 80 is formed in a thin sheet shape thinner than the shock-absorbing member 90 (described later). The lining member 80 is installed such that, in order to reduce wrinkling of the upper exterior body 10, one of the surfaces is stuck to the rear surface (back surface) of the upper exterior body 10 by, for example, double-faced adhesive tape or the like. The lining member 80 is, for example, made of a resin material, such as polyethylene terephthalate, having flexibility so as to be flexible (bendable) in an operation direction (for example, push-down direction) of the power switch 406. The lining member 80 may be made from a thin metal sheet or the like.

The lining member 80 has a through-hole 80a in the thickness direction. The power switch 406 fits inside the through-hole 80a when the lining member 80 is viewed in plan. The through-hole 80a may be formed such that the circumference of the hole is completely closed or may be formed such that the circumference of the hole is not completely closed. The through-hole 80a of the lining member 80 is formed to such a size that is smaller than the outside diameter of a fingertip to avoid entry of the entire fingertip and that allows a ball of a fingertip to enter to push the power switch 406. More specifically, since there are variations in the outside diameter of a fingertip among individuals, the inside diameter of the through-hole 80a is, for example, desirably set within a range of 10 mm to 20 mm and more desirably set within a range of 13 mm to 16 mm. When the thickness of the upper exterior body 10 is thick (when, the thickness is greater than or equal to, for example, 2 mm), it is desirable to increase the inside diameter of the through-hole 80a in accordance with the thickness of the upper exterior body 10.

The shock-absorbing member 90 having shock-absorbing characteristics (cushioning characteristics) and formed in a sheet shape is disposed between the top surface (main surface) of the wiring substrate 40 and the lining member 80. The shock-absorbing member 90 is formed so as to be thicker than a level (height) from the mounting surface of the wiring substrate 40 for the power switch 406 mounted on the wiring substrate 40 and a level (height) from the mounting surface of the wiring substrate 40 for electronic components. The shock-absorbing member 90 is installed by being stuck to the other surface of the lining member 80 by using, for example, double-faced adhesive tape or the like.

The shock-absorbing member 90 has a through-hole 90a in the thickness direction. The power switch 406 fits inside the through-hole 90a when the shock-absorbing member 90 is viewed in plan. The through-hole (opening portion) 90a formed in the shock-absorbing member 90 is formed and disposed so as to fit inside the through-hole (opening portion) 80a formed in the lining member 80 when viewed in plan. In other words, the through-hole 90a of the shock-absorbing member 90 is formed so as to be smaller than the through-hole 80a of the lining member 80. Each of the through-hole 90a formed in the shock-absorbing member 90 and the through-hole 80a formed in the lining member 80 has a substantially circular shape (including, for example, an elliptical shape or the like) and is set (formed) such that the inside diameter is smaller than the outside diameter of a fingertip. More specifically, the inside diameter of the opening portion 90a of the shock-absorbing member 90 is, for example, desirably set within a range of 8 mm to 18 mm and more desirably set within a range of 11 mm to 14 mm. When the upper exterior body 10 is thick (for example, thicker than or equal to 2 mm), it is desirable that the inside diameter of the through-hole 90a be increased in accordance with the thickness.

The sticking member 60 includes a first adhesion layer 601, a vent layer 603, and a second adhesion layer 602. The first adhesion layer 601 is stuck to an outer-side surface of the lower exterior body 20. The vent layer 603 has air permeability (that is, a moisture permeable layer that allows passage of moisture) and is stuck to the first adhesion layer 601. The second adhesion layer 602 is stuck to the vent layer 603. Incidentally, when the core body thermometer 1 is stuck to skin and is used, skin irritation may be caused if sweat remains accumulated for a long period of time between the skin and the core body thermometer 1 (lower exterior body 20); however, stuffiness due to sweat or the like is reduced by providing the sticking member 60 with the vent layer 603 that allows passage of moisture. For example, nonwoven fabric may be suitably used as the vent layer 603 (moisture permeable layer). Instead of nonwoven fabric, woven fabric or knitted fabric may be used. Alternatively, paper, wood, sponge/open cell foamed material, or the like may be used, or a plastic, rubber, or metal structure having a groove or hole extending from the center of the body temperature measurement unit 15 toward the periphery may be used.

The vent layer 603 contains air inside, so the vent layer 603 usually has a low thermal conductivity. Therefore, when the vent layer 603 is provided between skin and the core body thermometer 1, body temperature measurement accuracy is influenced. Therefore (to stably measure a body temperature), the vent layer 603 is not disposed in a region that overlaps the first temperature sensor 701 and the third temperature sensor 703 that measure the temperature of skin, and the heat equalizing pattern connected to them.

Here, description will be made by way of an example in which nonwoven fabric is used as the vent layer 603. Two pieces of biocompatible double-faced adhesive tape (the first adhesion layer 601 and the second adhesion layer 602) are respectively stuck to both surfaces of the nonwoven fabric (vent layer 603). Through-holes 60a, 60b are respectively formed in the vent layer 603 and the second adhesion layer 602 in the thickness direction. The first temperature sensor 701 and the third temperature sensor 703 respectively fit within the through-holes 60a, 60b when viewed in plan. Here, it is desirable that no through-hole is formed in the double-faced adhesive tape (first adhesion layer 601) stuck to the lower exterior body 20. This is because, when a through-hole is formed (that is, when no first adhesion layer 601 is provided), there are concerns that the lower exterior body 20 does not closely contact with skin and, as a result, measurement accuracy decreases.

Ordinarily, the double-faced adhesive tape (second adhesion layer 602) has a lower moisture permeability than the nonwoven fabric (vent layer 603), so it is desirable that a plurality of through-holes 60c formed in the thickness direction be formed in at least the second adhesion layer 602. In this case, it is desirable that, for example, the through-holes 60c having a diameter of about 1 to 10 mm be disposed at intervals of about 2 to 20 mm.

As described above, the calculation processing unit 43 (calculation processing circuit) is made up of, for example, an MCU (micro control unit), EEPROM, RAM, and the like.

The calculation processing unit 43 calculates a core body temperature in accordance with detected values (temperature data) of the temperature sensors 70, read via the temperature input unit 42 (temperature input circuit). The calculation processing unit 43 causes memory, such as the RAM, to store the calculated core body temperature data and the like. In addition, the calculation processing unit 43 wirelessly outputs (transmits) the calculated core body temperature data, the attachment/detachment information, and the like to the external management device and management system, or the like by outputting the calculated core body temperature data and the like to the wireless communication unit 403.

Particularly, the calculation processing unit 43 has a function of improving core body temperature measurement accuracy. Therefore, the calculation processing unit 43 functionally includes a correction value acquisition unit 431 and a core body temperature acquisition unit 432. In the calculation processing unit 43, the functions of the correction value acquisition unit 431 and core body temperature acquisition unit 432 are implemented by the MCU running programs stored in the EEPROM or the like.

Initially, a configuration to obtain a core body temperature by using a first temperature (T1) and a second temperature (T2) selected from among a first temperature (T1) detected by the first temperature sensor 701, a second temperature (T2) detected by the second temperature sensor 702, a third temperature (T3) detected by the third temperature sensor 703, and a fourth temperature (T4) detected by the fourth temperature sensor 704 will be described.

The correction value acquisition unit 431 obtains a first correction value that is a correction value used to correct the first temperature, in accordance with, for example, a first differential value (T0−T1) that is a differential value between the first temperature (T1) and a reference temperature (T0) set in advance to a temperature higher than the first temperature (T1) according to a limit body temperature up to which a body temperature feedback mechanism of a body works.

Here, the reference temperature (T0) is set by, for example, a first temperature (T1) and a core body temperature that are actually measured under conditions in which a body temperature increases, such as exercise, and in accordance with a relationship between both (that is, making a comparison between the measured values of the first temperature (T1) and core body temperature). After that, the reference temperature (T0) is desirably set to a value higher than or equal to a core body temperature during rest. In other words, the feedback of physiological response associated with thermoregulation by sweat and blood flow also works even when the core body temperature increases during exercise or the like as compared to during rest, so the reference temperature (T0) is desirably set to a value higher than or equal to a core body temperature during rest. Therefore, the reference temperature (T0) is desirably set, for example, within the range of 39 to 50(° C.). Particularly, the reference temperature (T0) is more desirably set within the range of 40 to 45(° C.). This is because the reference temperature (T0) is regarded as an upper limit up to which the thermoregulation function of a living body works. In the present embodiment, the reference temperature (T0) is set to 42(° C.).

The correction value acquisition unit 431 sets a first correction value such that, in a range in which the first differential value (T0−T1) is greater than or equal to zero, the first correction value increases as the first differential value (T0−T1) increases and a rate of increase (slope) in the first correction value increases as the first differential value (T0−T1) increases.

Figure 4:
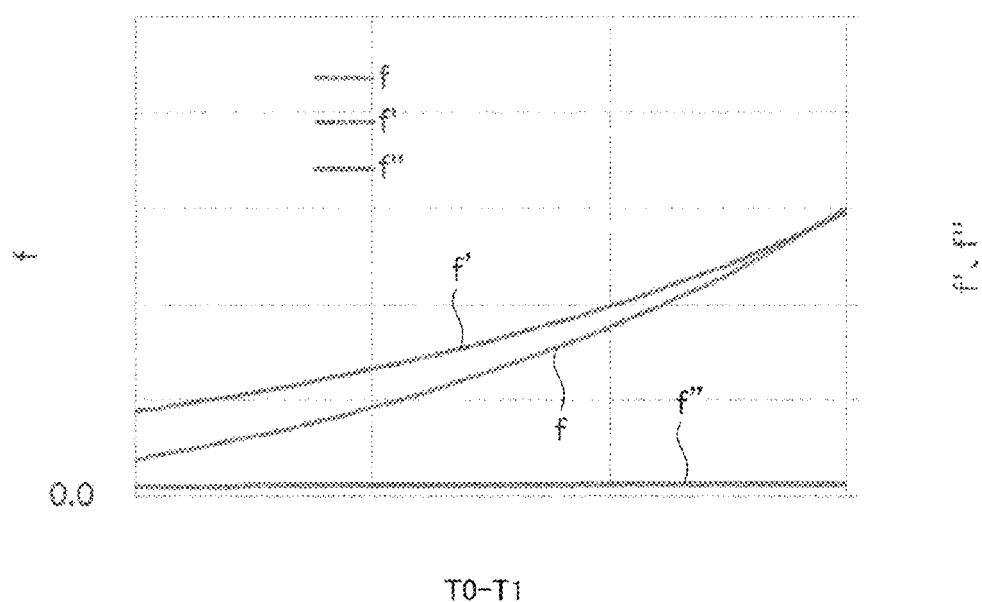
FIG. 4 is a graph showing an example of a first function (f) used to obtain a correction value.

At this time, the correction value acquisition unit 431, for example, obtains a first correction value (f(T0−T1)) from the first differential value (T0−T1) with a first function f that defines the relationship between first differential value (T0−T1) and first correction value as shown in FIG. 4. The first function f is a function of which, in the range in which the first differential value (T0−T1) is greater than or equal to zero, a first derivative f' is greater than or equal to zero and a second derivative f" is greater than or equal to zero. For example, an exponential function, a quadric function, a cubic function, a quartic function, or the like may be used as the first function f.

The correction value acquisition unit 431 obtains a second correction value that is a correction value used to correct the first temperature, in accordance with a second differential value (T1−T2) that is a differential value between the first temperature (T1) and the second temperature (T2).

The correction value acquisition unit 431 sets a second correction value such that, in a range in which the second differential value (T1−T2) is greater than or equal to zero, the second correction value increases as the second differential value (T1−T2) increases and a rate of increase (slope) in the second correction value decreases as the second differential value (T1−T2) increases.

Figure 5:
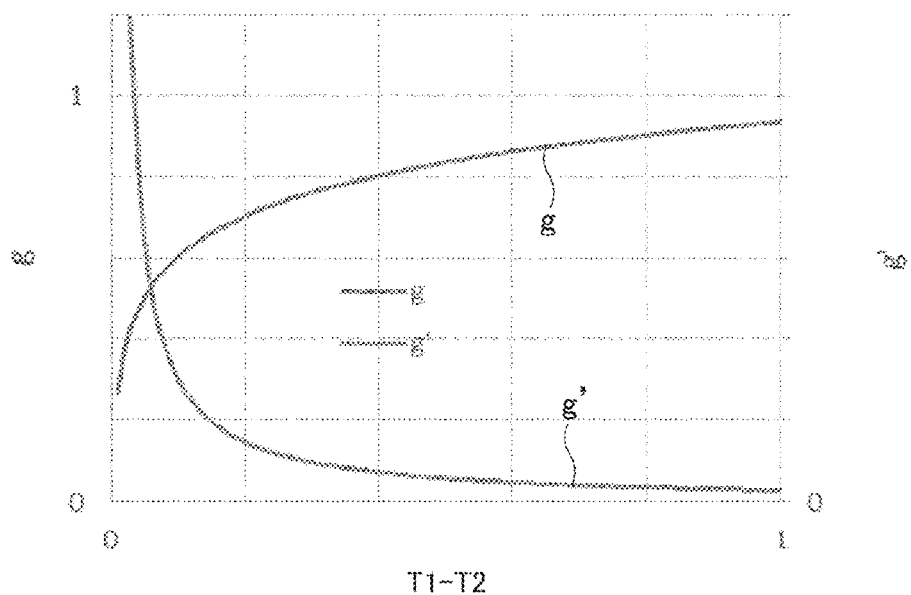
FIG. 5 is a graph showing an example of a second function (g) used to obtain a correction value.

At this time, the correction value acquisition unit 431, for example, obtains a second correction value (g(T1−T2)) from the second differential value (T1−T2) with a second function g that defines the relationship between second differential value (T1−T2) and second correction value as shown in FIG. 5. The second function g is a function of which, in the range in which the second differential value (T1−T2) is greater than or equal to zero, a first derivative g' is greater than or equal to zero and a second derivative g" is less than or equal to zero. When, for example, body temperature or ambient temperature fluctuates, the body temperature or ambient temperature is in a transient state for about 10 minutes to 20 minutes, so the transient characteristics of the second function g are corrected. For example, a logarithmic function, a square root function, or the like may be used as the second function g.

Look-up tables may be used instead of the function f and the function g to acquire correction values (a first correction value and a second correction value). In other words, a map that defines the relationship between first differential value (T0−T1) and first correction value (that is, a first correction value map in which an associated first correction value is given for each lattice point of the first differential value (T0−T1)) may be stored in advance in the EEPROM or the like (storage unit), and a first correction value may be obtained by looking up the first correction value map in accordance with the first differential value (T0−T1).

Similarly, a map that defines the relationship between second differential value (T1−T2) and second correction value (that is, a second correction value map in which an associated second correction value is given for each lattice point of the second differential value (T1−T2)) may be stored in advance in the EEPROM or the like (storage unit), and a second correction value may be obtained by looking up the second correction value map in accordance with the second differential value (T1−T2). The obtained correction values (the first correction value and the second correction value) are output to the core body temperature acquisition unit 432.

The core body temperature acquisition unit 432 obtains a core body temperature by correcting the first temperature (T1) by using the first correction value (f(T0−T1)) and the second correction value (g(T1−T2)). More specifically, the core body temperature acquisition unit 432 calculates a core body temperature in accordance with, for example, the following expression 1.

Core body temperature=First temperature (T1)+First correction value (f(T0−T1))×Second correction value (g(T1−T2))    (1)

Alternatively, the core body temperature acquisition unit 432 may obtain a core body temperature in accordance with the following expression 2.

Core body temperature=First temperature (T1)+First correction value (f(T0−T1))+Second correction value (g(T1−T2))    (2)

Figure 6:
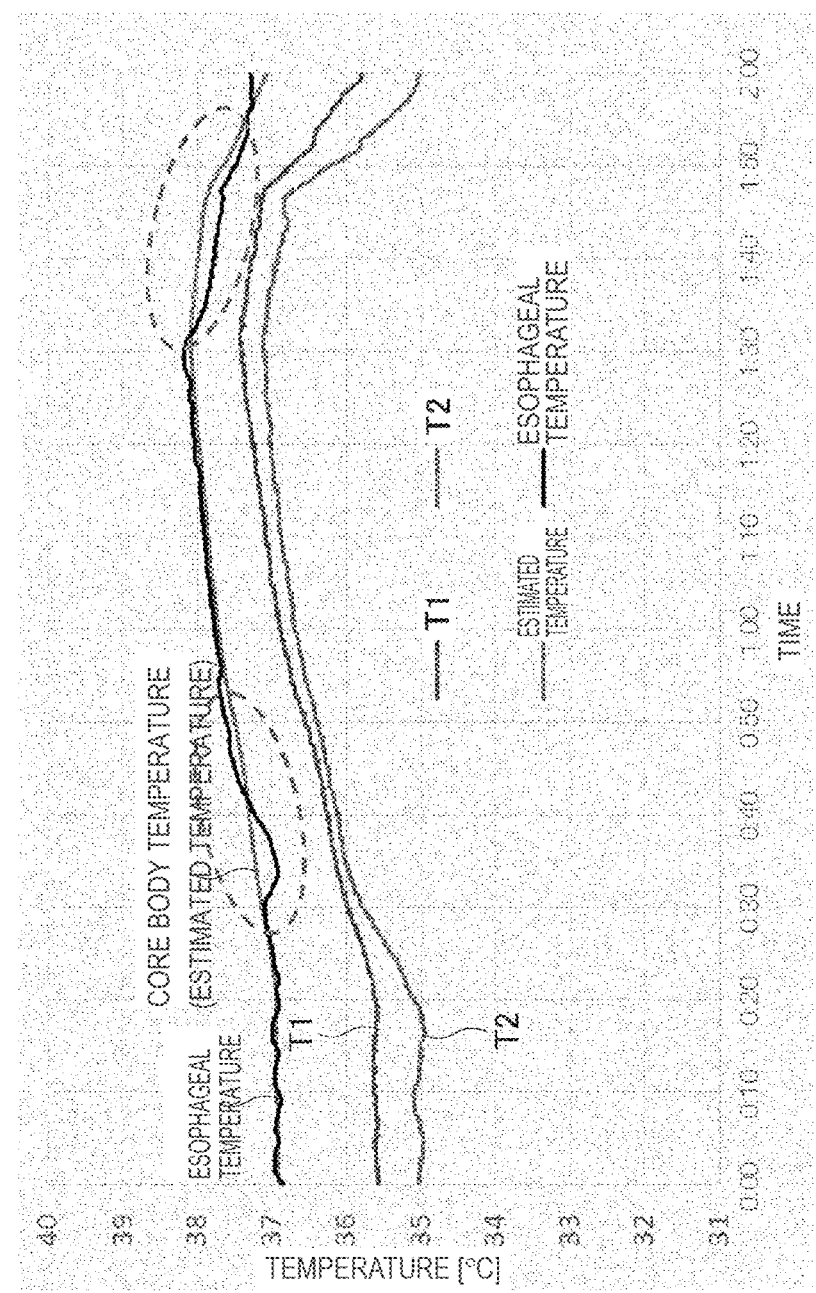
FIG. 6 is a graph showing an example of measurement results of first temperature (T1), second temperature (T2), core body temperature (estimated value), and esophageal temperature.

Here, an example of actually measured results is shown in FIG. 6. FIG. 6 is a graph showing an example of measurement results of first temperature (T1), second temperature (T2), core body temperature (estimated value), and esophageal temperature. In FIG. 6, the abscissa axis represents time, and the ordinate axis represents temperature (° C.). In the example of FIG. 6, the body temperature was increased by being placed under a high room temperature condition from a time point of 15 minutes to a time point of 1 hour 45 minutes and walking from a time point of 30 minutes to a time point of 1 hour 30 minutes, and the temperatures were measured. In other words, the core body thermometer 1 was stuck to the body to make measurement, while a temperature sensor was inserted to esophagus through the nose to measure the esophageal temperature recognized as core body temperature. As shown in FIG. 6, even when the body temperature increases and the gap between the first temperature (T1) and the second temperature (T2) is narrow, the corrected core body temperature (estimated value) and the esophageal temperature substantially coincide with each other, so it is confirmed that correction is effectively functioning.

Figure 7:
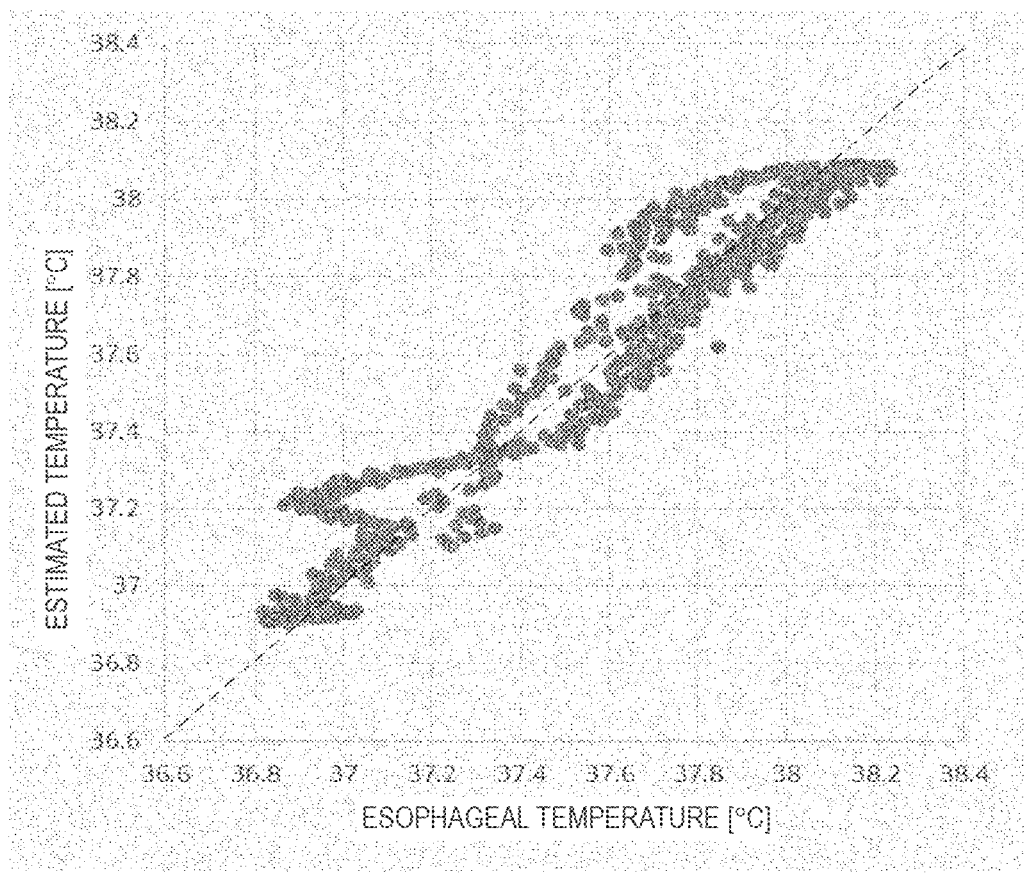
FIG. 7 is a graph showing an example of a relationship (correlation) between core body temperature (estimated value) and esophageal temperature.

FIG. 7 shows a graph in which corresponding points of the core body temperatures (estimated values) and the esophageal temperatures, shown in FIG. 6, are plotted. In FIG. 7, the abscissa axis represents esophageal temperature (° C.), and the ordinate axis represents core body temperature (estimated value) (° C.). As shown in FIG. 7, it is confirmed that the corrected core body temperature (estimated value) and the esophageal temperature have a high correlation.

As described in detail above, according to the present embodiment, by using the first differential value (T0−T1) between the reference temperature (T0) set in advance according to a limit body temperature up to which the body temperature feedback mechanism of the body works and the first temperature (T1) on the sticking surface side (body surface side) as a parameter, when, for example, the first temperature (body surface temperature) increases with an increase in heat radiation from the body surface and, as a result, the body surface temperature approaches a core body temperature, the first differential value reduces. In this case, measurement accuracy is improved by reducing the correction value. On the other hand, when the first temperature (body surface temperature) decreases with a reduction in heat radiation from the body surface and, as a result, the body surface temperature deviates from the core body temperature, the first differential value increases. In this case, measurement accuracy is improved by increasing the correction value. In this way, physiological response associated with thermoregulation by sweat and blood flow can be considered, so consistency with an actual body temperature is enhanced. Thus, a core body temperature is highly accurately obtained with relatively simple calculation.

According to the present embodiment, the second differential value (T1−T2) has a correlation with heat flux, so measurement accuracy is further improved by adding the second correction value (g(T1−T2)). Incidentally, when moved to a place where outside air temperature is sufficiently lower than the core body temperature (for example, an outside air temperature of 20° C.), the first temperature (T1) also decreases under the influence of outside air temperature. In this case, heat flux increases, so the second differential value (T1−T2) increases. When rapid heat generation (increase in core body temperature) occurs due to exercise or the like, heat flux increases, and the second differential value (T1−T2) increases. When the second differential value (T1−T2) is large, the second correction value (g(T1−T2)) increases to improve estimation accuracy. In addition, when the second function g is set to a function of which the second derivative g″≤0, that is, the second correction value (g(T1−T2)) increases with an increase in second differential value (T1−T2); however, the influence of the case where the second differential value (T1−T2) excessively increases is suppressed by a decreased rate of increase.

First Modification of First Embodiment

Figure 8:
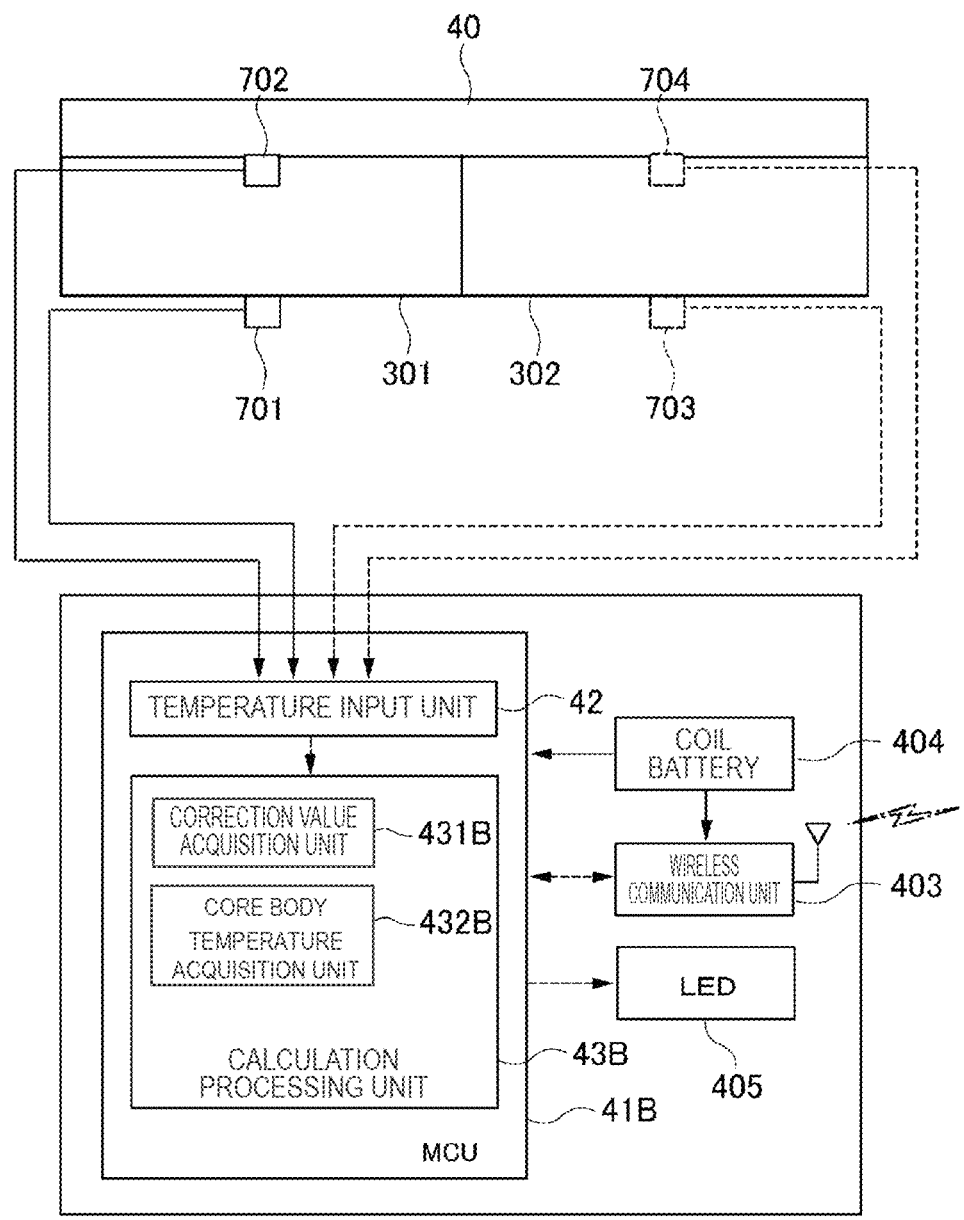
FIG. 8 is a block diagram showing the functional configuration of a processing unit that is a component of a sticking-type core body thermometer according to a first modification of the first embodiment.

Next, a core body thermometer 1B according to a first modification of the first embodiment will be described with reference to FIG. 8. Here, the description of components identical or similar to those of the above-described first embodiment is simplified or omitted, and differences will be mainly described. FIG. 8 is a block diagram showing the functional configuration of a processing unit 41B that is a component of the sticking-type core body thermometer 1B according to the first modification of the first embodiment. Like reference signs denote identical or similar components to those of the first embodiment in FIG. 8.

The core body thermometer 1B differs from the above-described core body thermometer 1 in that the core body thermometer 1B includes the processing unit 41B instead of the processing unit 41. The processing unit 41B differs from the above-described processing unit 41 in that the processing unit 41B includes a correction value acquisition unit 431B and a core body temperature acquisition unit 432B instead of the correction value acquisition unit 431 and the core body temperature acquisition unit 432. The other configuration is identical or similar to that of the core body thermometer 1, so the detailed description is omitted here.

The correction value acquisition unit 431B obtains the above-described first correction value (f(T0−T1)). A method of acquiring the first correction value (f(T0−T1)) is as described above, so the detailed description is omitted here. The correction value acquisition unit 431B acquires a fourth correction value instead of the above-described second correction value (g(T1−T2)). More specifically, the correction value acquisition unit 431B further obtains a third correction value (sub-correction value) used to correct the second differential value (T1−T2), in accordance with a time change in first temperature (T1) (differential value ΔT1), and obtains a fourth correction value used to correct the first temperature T1 in accordance with a corrected second differential value corrected by using the third correction value (that is, in accordance with the second differential value and the third correction value).

More specifically, the correction value acquisition unit 431B sets a third correction value such that the third correction value (sub-correction value) increases as the amount of increase per unit time in first temperature (T1) (differential value ΔT1) increases, and sets a fourth correction value such that the fourth correction value increases as a corrected second differential value corrected by using the third correction value increases and the rate of increase (slope) in second correction value decreases as a corrected second differential value increases.

For example, initially, the correction value acquisition unit 431B obtains a third correction value (k(ΔT1)) from a time change in first temperature (T1) (differential value ΔT1) with a third function k that defines the relationship between time change in first temperature (T1) (differential value ΔT1) and third correction value (k(ΔT1)). Subsequently, the correction value acquisition unit 431B obtains a fourth correction value (g(T1−T2+k(ΔT1))) from a corrected second differential value (T1−T2+k(ΔT1)) with a fourth function g that defines the relationship between fourth correction value and corrected second differential value (T1−T2+k(ΔT1)) corrected by using the third correction value (k(ΔT1)).

Here, the third function k is a function that monotonously increases with an increase in the amount of increase per unit time in first temperature (T1) (differential value ΔT1). The third function k effectively works at the measurement start at which temperature rapidly varies, for example, just after the core body thermometer 1B is stuck to the body surface, and further improves measurement accuracy. The above-described second function g may be used as the fourth function. In other words, the fourth function g is a function of which, in the range in which the corrected second differential value is greater than or equal to zero, a first derivative g' is greater than or equal to zero and a second derivative g" is less than or equal to zero.

Incidentally, the core body thermometer 1B has a thermal capacity, so there is a time lag in temperature change between the first temperature (T1) and the second temperature (T2). Therefore, accuracy is further improved by adding a term ΔT1 that correlates with the time lag to the expression. When, for example, the outside air temperature increases, heat flux from outside air increases, with the result that the second temperature (T2) increases first and then the first temperature (T1) increases (ΔT1>0). For this reason, the second differential value (T1−T2) reduces. Although the core body temperature remains unchanged, the estimated value decreases due to a decrease in second differential value (T1−T2). Therefore, a decrease in estimated value is suppressed by making a correction according to ΔT1. The reason why a time change ΔT1 in first temperature (T1) is used as a correction method is because a time lag increases as a temperature rate of change increases. Thus, a decrease in the accuracy of core body temperature (estimated value) is suppressed. On the other hand, when the outside air temperature decreases, heat flux from outside air decreases, so T2 decreases first and then the first temperature (T1) decreases (ΔT1<0). For this reason, the second differential value (T1−T2) increases. Although the core body temperature remains unchanged, the estimated value increases due to an increase in second differential value (T1−T2). Therefore, an increase in estimated value is suppressed by making a correction according to ΔT1. When the body temperature increases, heat flux from the body surface increases, with the result that the first temperature (T1) increases first (ΔT1>0) and then the second temperature (T2) increases. For this reason, the second differential value (T1−T2) increases. However, since the core body temperature increases first, a large deviation does not occur even when an increase in the estimated value due to an increase in second differential value (T1−T2) is considered. On the other hand, when the body temperature decreases, heat flux from the body surface decreases, so the first temperature (T1) decreases first (ΔT1<0) and then the second temperature (T2) decreases. For this reason, the second differential value (T1−T2) reduces. However, since the core body temperature decreases first, a large deviation does not occur even when a decrease in the estimated value due to a decrease in second differential value (T1−T2) is considered.

Look-up tables may be used instead of the function k and the function g to acquire correction values (a third correction value and a fourth correction value). In other words, a map that defines the relationship between time change in first temperature (T1) (differential value ΔT1) and third correction value (that is, a third correction value map in which an associated third correction value is given for each lattice point of the time change in first temperature (T1) (differential value ΔT1)) may be stored in advance in the EEPROM or the like (storage unit), and a third correction value may be obtained by looking up the third correction value map in accordance with the time change in first temperature (T1) (differential value ΔT1). Similarly, a map that defines the relationship between corrected second differential value (T1−T2+k(ΔT1)) and fourth correction value (that is, a fourth correction value map in which an associated fourth correction value is given for each lattice point of the corrected second differential value (T1−T2+k(ΔT1)) may be stored in advance in the EEPROM or the like (storage unit), and a fourth correction value may be obtained by looking up the fourth correction value map in accordance with the corrected second differential value (T1−T2+k(ΔT3)). The obtained correction values (the first correction value and the fourth correction value) are output to the core body temperature acquisition unit 432B.

The core body temperature acquisition unit 432B obtains a core body temperature by correcting the first temperature (T1) by using the first correction value (f(T0−T1)) and the fourth correction value (g(T1−T2+k(ΔT1))). For example, the core body temperature acquisition unit 432B calculates a core body temperature in accordance with, for example, the following expression 3.

Core body temperature=First temperature (T1)+First correction value (f(T0−T1))×Fourth correction value (g(T1−T2+k(ΔT1))) (3)

Alternatively, the core body temperature acquisition unit 432B may obtain a core body temperature in accordance with the following expression 4.

Core body temperature=First temperature (T1)+First correction value (f(T0−T1))+Fourth correction value (g(T1−T2+k(ΔT1))) (4)

According to the present modification, measurement accuracy is improved by further considering the term ΔT1 having a correlation with a time lag between the first temperature (T1) and the second temperature (T2) (that is, a delay of temperature change) caused by the thermal capacity of the core body thermometer 1B.

Second Modification of First Embodiment

Figure 9:
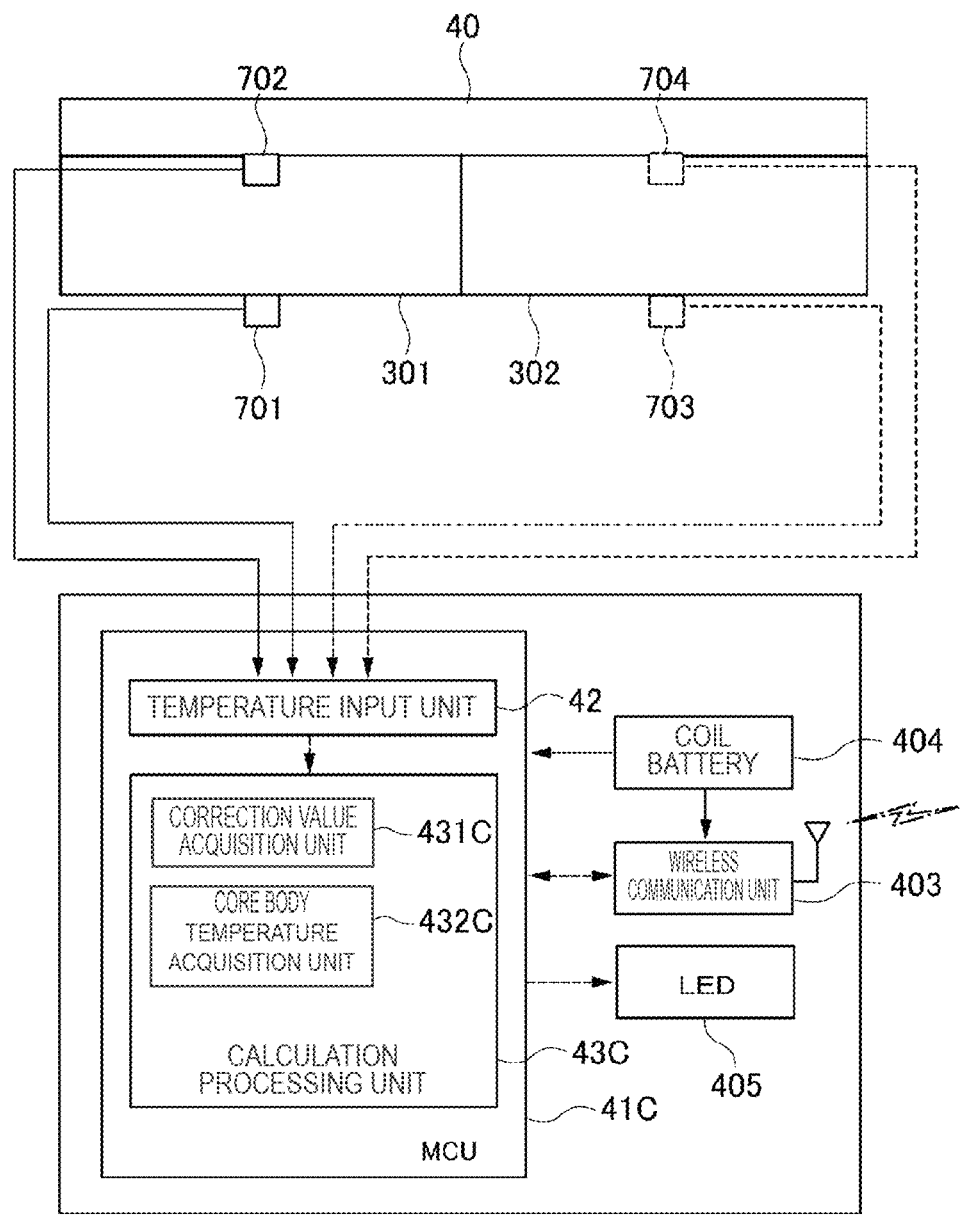
FIG. 9 is a block diagram showing the functional configuration of a processing unit that is a component of a sticking-type core body thermometer according to a second modification of the first embodiment.

Next, a core body thermometer 1C according to a second modification of the first embodiment will be described with reference to FIG. 9. Here, the description of components identical or similar to those of the above-described first embodiment is simplified or omitted, and differences will be mainly described. FIG. 9 is a block diagram showing the functional configuration of a processing unit 41C that is a component of the sticking-type core body thermometer 1C according to the second modification of the first embodiment. Like reference signs denote identical or similar components to those of the first embodiment in FIG. 9.

The core body thermometer 1C differs from the above-described core body thermometer 1 in that the core body thermometer 1C includes the processing unit 41C instead of the processing unit 41. The processing unit 41C differs from the above-described processing unit 41 in that the processing unit 41C includes a correction value acquisition unit 431C and a core body temperature acquisition unit 432C instead of the correction value acquisition unit 431 and the core body temperature acquisition unit 432. The other configuration is identical or similar to that of the core body thermometer 1, so the detailed description is omitted here.

The correction value acquisition unit 431C obtains the above-described first correction value (f(T0−T1)). A method of acquiring the first correction value (f(T0−T1)) is as described above, so the detailed description is omitted here. The correction value acquisition unit 431C acquires a fifth correction value instead of the above-described second correction value (g(T1−T2)). More specifically, the correction value acquisition unit 431C obtains a fifth correction value that is a correction value used to correct the first temperature T1, in accordance with a third differential value (T0−T2) that is a differential value between the reference temperature (T0) and the second temperature (T2).

For example, the correction value acquisition unit 431C sets a fifth correction value such that, in a range in which the third differential value (T0−T2) is greater than or equal to zero, the fifth correction value increases as the third differential value (T0−T2) increases and the rate of increase (slope) in the fifth correction value decreases as the third differential value (T0−T2) increases.

More specifically, the correction value acquisition unit 431C obtains a fifth correction value from the third differential value (T0−T2) with a fifth function g that defines the relationship between third differential value (T0−T2) and fifth correction value. The above-described second function g may be used as the fifth function. In other words, the fifth function g is a function of which, in the range in which the third differential value (T0−T2) is greater than or equal to zero, a first derivative g' is greater than or equal to zero and a second derivative g'' is less than or equal to zero.

A map (look-up table) may be used instead of the function g to acquire a correction value (a fifth correction value). In other words, a map that defines the relationship between third differential value (T0−T2) and fifth correction value (that is, a fifth correction value map in which an associated fifth correction value is given for each lattice point of the third differential value (T0−T2)) may be stored in advance in the EEPROM or the like (storage unit), and a fifth correction value may be obtained by looking up the fifth correction value map in accordance with the third differential value (T0−T2). The obtained correction values (the first correction value and the fifth correction value) are output to the core body temperature acquisition unit 432C.

The core body temperature acquisition unit 432C obtains a core body temperature by correcting the first temperature (T1) by using the first correction value (f(T0−T1)) and the fifth correction value (g(T0−T2)). For example, the core body temperature acquisition unit 432C calculates a core body temperature in accordance with, for example, the following expression 5.

$$\text{Core body temperature} = \text{First temperature }(T1) + \text{First correction value }(f(T0-T1)) \times \text{Fifth correction value }(g(T0-T2)) \qquad (5)$$

Alternatively, the core body temperature acquisition unit 432C may obtain a core body temperature in accordance with the following expression 6.

$$\text{Core body temperature} = \text{First temperature }(T1) + \text{First correction value }(f(T0-T1)) + \text{Fifth correction value }(g(T0-T2)) \qquad (6)$$

According to the present modification, the third differential value (T0−T2) is used instead of the second differential value (T1−T2), so a core body temperature is accurately estimated even when heat flux is small (that is, when a temperature difference between the first temperature (T1) and the second temperature (T2) is small).

Third Modification of First Embodiment

Figure 10:
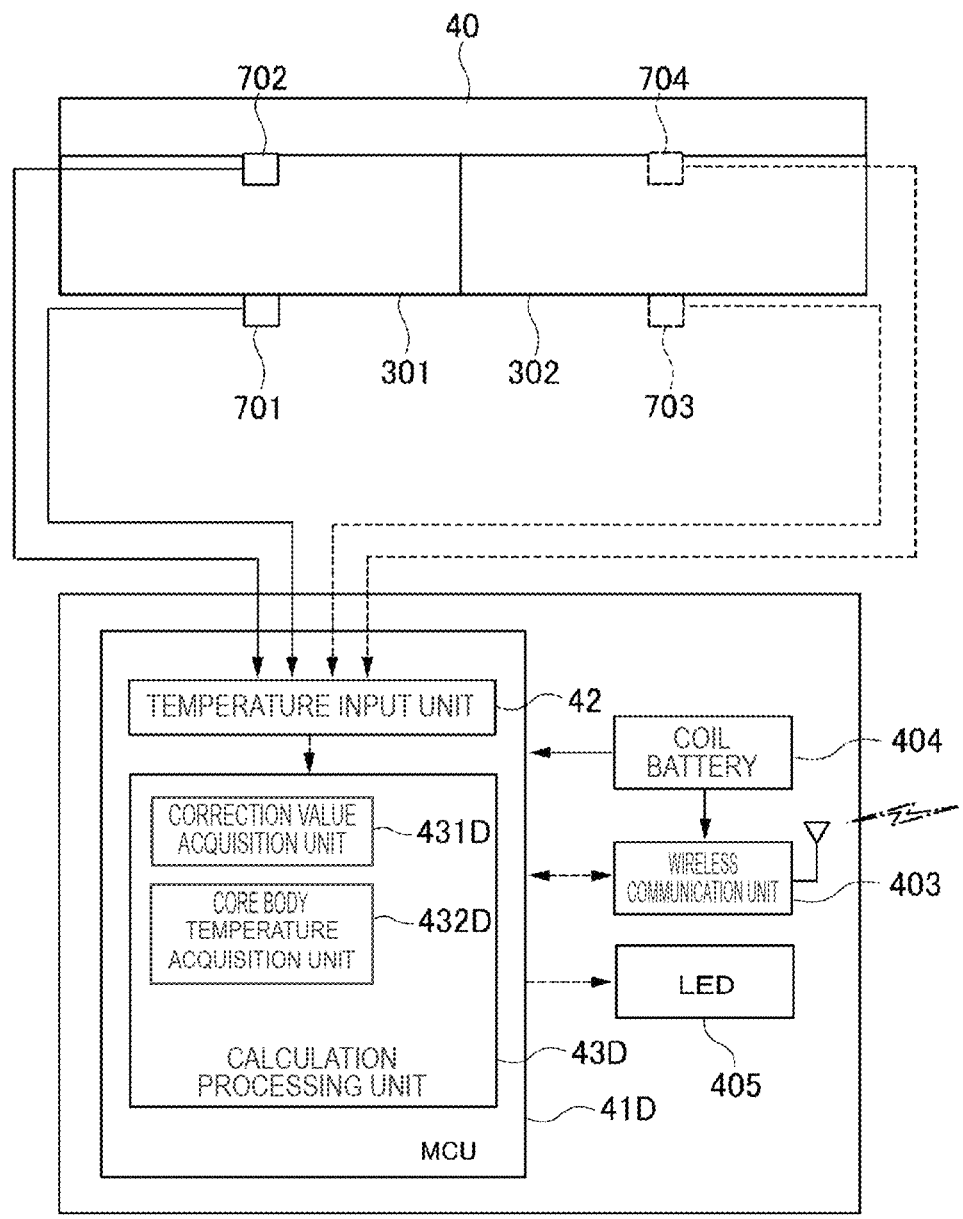
FIG. 10 is a block diagram showing the functional configuration of a processing unit that is a component of a sticking-type core body thermometer according to a third modification of the first embodiment.

Next, a core body thermometer 1D according to a third modification of the first embodiment will be described with reference to FIG. 10. Here, the description of components identical or similar to those of the above-described first embodiment is simplified or omitted, and differences will be mainly described. FIG. 10 is a block diagram showing the functional configuration of a processing unit 41D that is a component of the sticking-type core body thermometer 1D according to the third modification of the first embodiment. Like reference signs denote identical or similar components to those of the first embodiment in FIG. 10.

The core body thermometer 1D differs from the above-described core body thermometer 1 in that the core body thermometer 1D includes the processing unit 41D instead of the processing unit 41. The processing unit 41D differs from the above-described processing unit 41 in that the processing unit 41D includes a correction value acquisition unit 431D and a core body temperature acquisition unit 432D instead of the correction value acquisition unit 431 and the core body temperature acquisition unit 432. The other configuration is identical or similar to that of the core body thermometer 1, so the detailed description is omitted here.

The correction value acquisition unit 431D obtains a seventh correction value instead of the above-described first correction value. More specifically, the correction value acquisition unit 431D obtains a sixth correction value (sub-correction value) used to correct the first differential value (T0−T1), in accordance with a time change in first temperature (T1) (differential value ΔT1), and obtains a seventh correction value used to correct the first temperature, in accordance with a corrected first differential value corrected by using the sixth correction value (in accordance with the first differential value and the sixth correction value). The correction value acquisition unit 431D obtains a ninth correction value instead of the above-described second correction value. More specifically, the correction value acquisition unit 431D obtains an eighth correction value (sub-correction value) used to correct the third differential value (T0−T2), in accordance with a time change in second temperature (T2) (differential value ΔT2), and obtains a ninth correction value used to correct the first temperature, in accordance with a corrected third differential value corrected by using the eighth correction value (in accordance with the third differential value and the eighth correction value).

More specifically, the correction value acquisition unit 431D sets a sixth correction value such that the sixth correction value (sub-correction value) increases as the amount of increase per unit time in first temperature (T1) (differential value $\Delta T1$) increases, and sets a seventh correction value such that the seventh correction value increases as the corrected first differential value corrected by using the sixth correction value increases and the rate of increase (slope) in seventh correction value increases as the corrected first differential value increases. More specifically, the correction value acquisition unit 431D sets an eighth correction value such that the eighth correction value (sub-correction value) increases as the amount of increase per unit time in second temperature (T2) (differential value $\Delta T2$) increases, and sets a ninth correction value such that the ninth correction value increases as the corrected third differential value corrected by using the eighth correction value increases and the rate of increase (slope) in ninth correction value decreases as the corrected third differential value increases.

For example, the correction value acquisition unit 431D obtains a sixth correction value (h($\Delta T1$)) from a time change in first temperature (T1) (differential value $\Delta T1$) with a sixth function h that defines the relationship between time change in first temperature (T1) (differential value $\Delta T1$) and sixth correction value (h($\Delta T1$)), and obtains a seventh correction value (f(T0−T1+h($\Delta T1$))) from a corrected first differential value (T0−T1+h($\Delta T1$)) with a seventh function f that defines the relationship between seventh correction value and corrected first differential value (T0−T1+h($\Delta T1$)) corrected by using the sixth correction value (h($\Delta T1$)). The correction value acquisition unit 431D obtains an eighth correction value (k($\Delta T2$)) from a time change in second temperature (T2) (differential value $\Delta T2$) with an eighth function k that defines the relationship between time change in second temperature (T2) (differential value $\Delta T2$) and eighth correction value (k($\Delta T2$), and obtains a ninth correction value (g(T0−T2+k($\Delta T2$))) from a corrected third differential value with a ninth function g that defines the relationship between ninth correction value and corrected third differential value (T0−T2+k($\Delta T2$)) corrected by using the eighth correction value (k($\Delta T2$)).

Here, the sixth function h is a function that monotonously increases with an increase in the amount of increase per unit time in first temperature (T1) (differential value $\Delta T1$). Similarly, the eighth function k is a function that monotonously increases with an increase in the amount of increase per unit time in second temperature (T2) (differential value $\Delta T2$). The above-described first function f may be used as the seventh function. The above-described second function g may be used as the ninth function.

Look-up tables may be used instead of the functions (arithmetic expressions) h, f to acquire correction values (sixth and seventh correction values). In other words, a map that defines the relationship between time change in first temperature (T1) (differential value $\Delta T1$) and sixth correction value (that is, a sixth correction value map in which an associated sixth correction value is given for each lattice point of the time change in first temperature (T1) (differential value $\Delta T1$) may be stored in advance in the EEPROM or the like (storage unit), and a sixth correction value may be obtained by looking up the sixth correction value map in accordance with the time change in first temperature (T1) (differential value $\Delta T1$). Similarly, a map that defines the relationship between corrected first differential value and seventh correction value (that is, a seventh correction value map in which an associated seventh correction value is given for each lattice point of the corrected first differential value may be stored in advance in the EEPROM or the like (storage unit), and a seventh correction value may be obtained by looking up the seventh correction value map in accordance with a corrected first differential value.

Similarly, look-up tables may be used instead of the functions (arithmetic expressions) k, g to acquire correction values (eighth and ninth correction values). In other words, a map that defines the relationship between time change in second temperature (T2) (differential value $\Delta T2$) and eighth correction value (that is, an eighth correction value map in which an associated eighth correction value is given for each lattice point of the time change in second temperature (T2) (differential value $\Delta T2$)) may be stored in advance in the EEPROM or the like (storage unit), and an eighth correction value may be obtained by looking up the eighth correction value map in accordance with a time change in second temperature (T2) (differential value $\Delta T2$). Similarly, a map that defines the relationship between corrected third differential value and ninth correction value (that is, a ninth correction value map in which an associated ninth correction value is given for each lattice point of the corrected third differential value may be stored in advance in the EEPROM or the like (storage unit), and a ninth correction value may be obtained by looking up the ninth correction value map in accordance with a corrected third differential value. The obtained correction values (the seventh correction value and the ninth correction value) are output to the core body temperature acquisition unit 432D.

The core body temperature acquisition unit 432D obtains a core body temperature by correcting the first temperature (T1) by using the seventh correction value (f(T0−T1+h($\Delta T1$))) and the ninth correction value (g(T0−T2+k($\Delta T2$))). For example, the core body temperature acquisition unit 432D calculates a core body temperature in accordance with, for example, the following expression 7.

$$\text{Core body temperature} = \text{First temperature }(T1) + \text{Seventh correction value }(f(T0-T1+h(\Delta T1))) \times \text{Ninth correction value }(g(T0-T2+k(\Delta T2))) \qquad (7)$$

Alternatively, the core body temperature acquisition unit 432D may obtain a core body temperature in accordance with the following expression 8.

$$\text{Core body temperature} = \text{First temperature }(T1) + \text{Seventh correction value }(f(T0-T1+h(\Delta T1))) + \text{Ninth correction value }(g(T0-T2+k(\Delta T2))) \qquad (8)$$

According to the present modification, measurement accuracy is improved by further considering the term $\Delta T2$ having a correlation with a time lag between the first temperature (T1) and the second temperature (T2) (that is, a delay of temperature change) caused by the thermal capacity of the core body thermometer 1D. Thus, a correlation with a core body temperature is further enhanced.

Fourth Modification of First Embodiment

Figure 11:
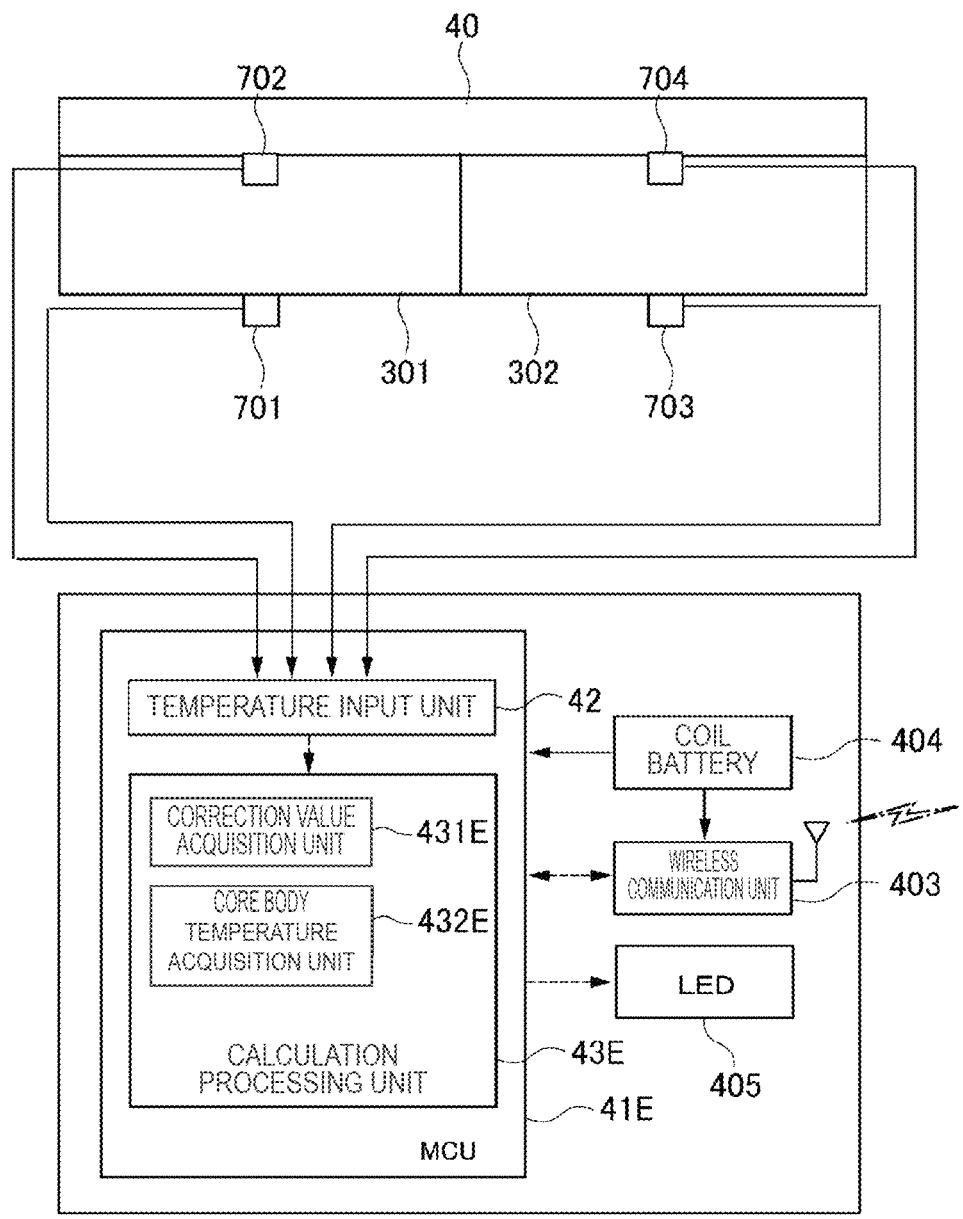
FIG. 11 is a block diagram showing the functional configuration of a processing unit that is a component of a sticking-type core body thermometer according to a fourth modification of the first embodiment.

Next, a core body thermometer 1E according to a fourth modification of the first embodiment will be described with reference to FIG. 11. Here, the description of components identical or similar to those of the above-described first embodiment is simplified or omitted, and differences will be mainly described. FIG. 11 is a block diagram showing the functional configuration of a processing unit 41E that is a component of the sticking-type core body thermometer 1E according to the fourth modification of the first embodiment. Like reference signs denote identical or similar components to those of the first embodiment in FIG. 11.

The core body thermometer 1E differs from the above-described core body thermometer 1 in that the core body thermometer 1E includes the processing unit 41E instead of the processing unit 41. The processing unit 41E differs from the above-described processing unit 41 in that the processing unit 41E includes a correction value acquisition unit 431E and a core body temperature acquisition unit 432E instead of the correction value acquisition unit 431 and the core body temperature acquisition unit 432. The other configuration is identical or similar to that of the core body thermometer 1, so the detailed description is omitted here.

The correction value acquisition unit 431E acquires the above-described correction values for each of two sensing units, that is, a sensing unit including the first thermal resistor 301, the first temperature sensor 701 (T1), and the second temperature sensor 702 (T2) and a sensing unit including the second thermal resistor 302, the third temperature sensor 703 (T3), and the fourth temperature sensor 704 (T4). Any of the above-described correction values (correction methods) may be adopted. A manner of obtaining the correction values is as described above, so the detailed description is omitted here. Acquired correction values are output to the core body temperature acquisition unit 432E.

The core body temperature acquisition unit 432E obtains two temporary core body temperatures (estimated values) by using the correction values for the respective two sensing units. Any of the above-described methods of obtaining a core body temperature may be adopted. The methods of obtaining a core body temperature are as described above, so the detailed description is omitted here. The core body temperature acquisition unit 432E determines a core body temperature in accordance with the two temporary core body temperatures and obtains the likelihood of the core body temperature.

In other words, the core body temperature acquisition unit 432E estimates a core body temperature from each of a set of the first temperature (T1) and the second temperature (T2) and a set of the third temperature (T3) and the fourth temperature (T4), determines a core body temperature from the core body temperatures (estimated values), and determines the likelihood of the core body temperature. Incidentally, when a stuck state is poor, for example, when the core body thermometer 1E is not in close contact with the body surface due to a large amount of sweat or body hair, the estimation accuracy of a core body temperature (estimated value) decreases. For this reason, the core body temperature acquisition unit 432E calculates two estimated temperatures, compares the two estimated temperatures, and determines that the likelihood of the estimated temperatures is low when the difference between the two is large. When the outside air temperature is lower than a body temperature (body surface temperature), that is, during normal times, the order in temperature T1>T3>T4≈T2 holds, so it may be determined that the likelihood is low when this order changes. When, for example, T3>T1>T4≈T2, the core body temperature acquisition unit 432E determines that the likelihood of the estimated temperature using the first temperature (T1) and the second temperature (T2) is low. When a stuck state is poor and the core body thermometer 1E is not in close contact with the body surface, variations in the first temperature (T1) or the third temperature (T3) with time increase, so it may be determined that the likelihood is low when a variation in the first temperature (T1) or the third temperature (T3) within a certain period of time exceeds a predetermined value. When it is determined that the likelihood is low, it is desirable to inform a user or the like of that effect by using, for example, the wireless communication unit 403. It is also desirable to inform by, for example, indication on a control terminal, voice, vibration, or the like. The core body temperature acquisition unit 432E improves the accuracy of estimated temperatures by processing two estimated values and determining an estimated temperature. Since estimated temperatures decrease when the stuck state of the core body thermometer 1E is poor, it is desirable to select a larger one of the two estimated temperatures. Alternatively, an average, a weighted average, or the like may also be used. When the outside air temperature is higher than the body temperature (body surface temperature), estimated temperatures increase when the stuck state is poor, so a smaller one is selected when the outside air temperature is higher than the body temperature (body surface temperature). Whether the outside air temperature is higher than the body temperature (body surface temperature) may be determined by adding a temperature sensor for measuring the outside air temperature and is desirably determined depending on whether T1−T2 is negative.

Figure 13:
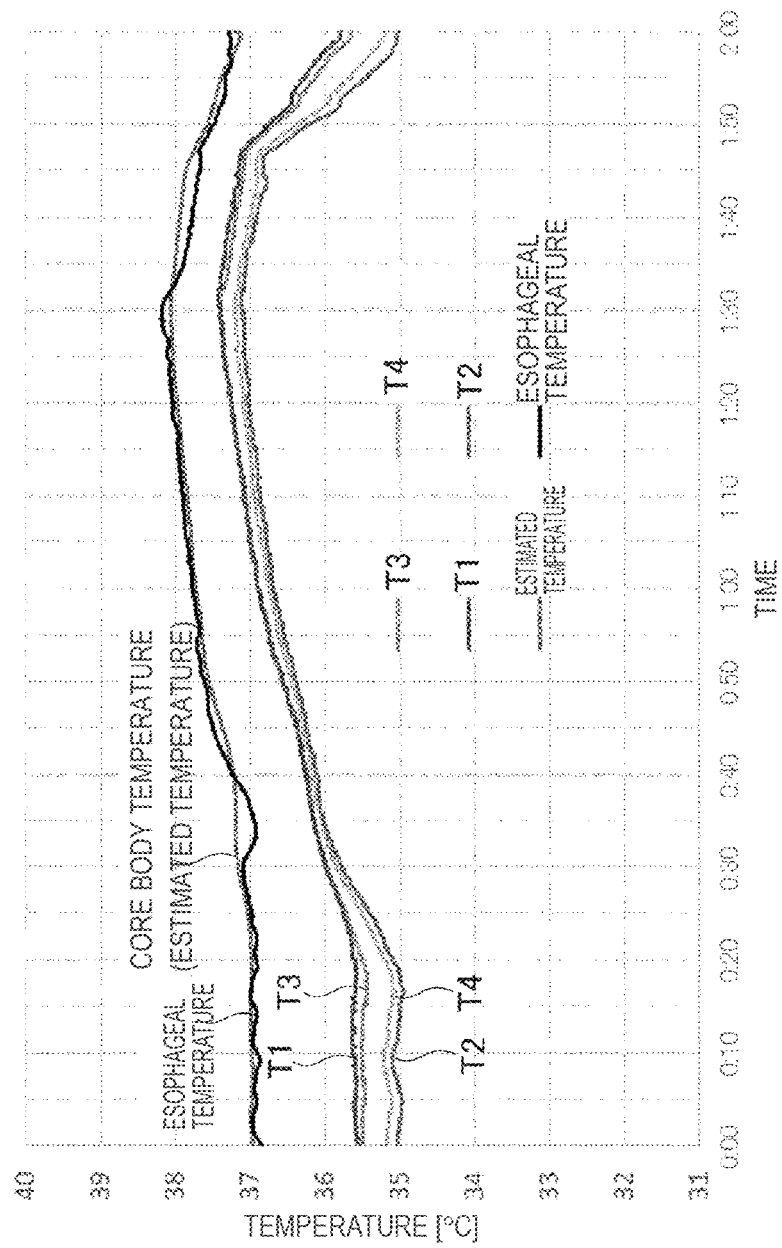
FIG. 13 is a graph showing an example of measurement results of first temperature (T1), second temperature (T2), third temperature (T3), fourth temperature (T4), core body temperature (estimated value), and esophageal temperature.

Here, an example of actually measured results is shown in FIG. 13. FIG. 13 is a graph showing an example of measurement results of first temperature (T1), second temperature (T2), third temperature (T3), fourth temperature (T4), core body temperature (estimated value), and esophageal temperature. In FIG. 13, the abscissa axis represents time, and the ordinate axis represents temperature (° C.). In the example of FIG. 13, the body temperature was increased by being placed under a high room temperature condition from a time point of 15 minutes to a time point of 1 hour 45 minutes and walking from a time point of 30 minutes to a time point of 1 hour 30 minutes, and the temperatures were measured. In other words, the core body thermometer 1E was stuck to the body to make measurement, while a temperature sensor was inserted to esophagus through the nose to measure the esophageal temperature recognized as core body temperature. As shown in FIG. 13, even when the body temperature increases and the gap between the first temperature (T1) and the second temperature (T2) and the gap between the third temperature (T3) and the fourth temperature (T4) are narrow, the corrected core body temperature (estimated value) and the esophageal temperature almost coincide with each other, so it is confirmed that correction is effectively functioning. In comparison with the measurement results shown in FIG. 6 (described above) or shown in FIG. 14 (described later) (particularly, the area indicated by the dotted ellipse in the graph), it is confirmed that the corrected core body temperature (estimated value) and the esophageal temperature almost coincide with each other.

According to the present modification, the likelihood of an estimated temperature may be determined by calculating two core body temperatures (estimated values) and making a comparison between both. When the likelihood is low, a user may be informed. In addition, the estimation accuracy of a core body temperature (estimated temperature) is improved by processing two estimated values (for example, taking an average, a maximum value, a minimum value, or a weighted average) and determining a core body temperature.

Second Embodiment

Figure 12:
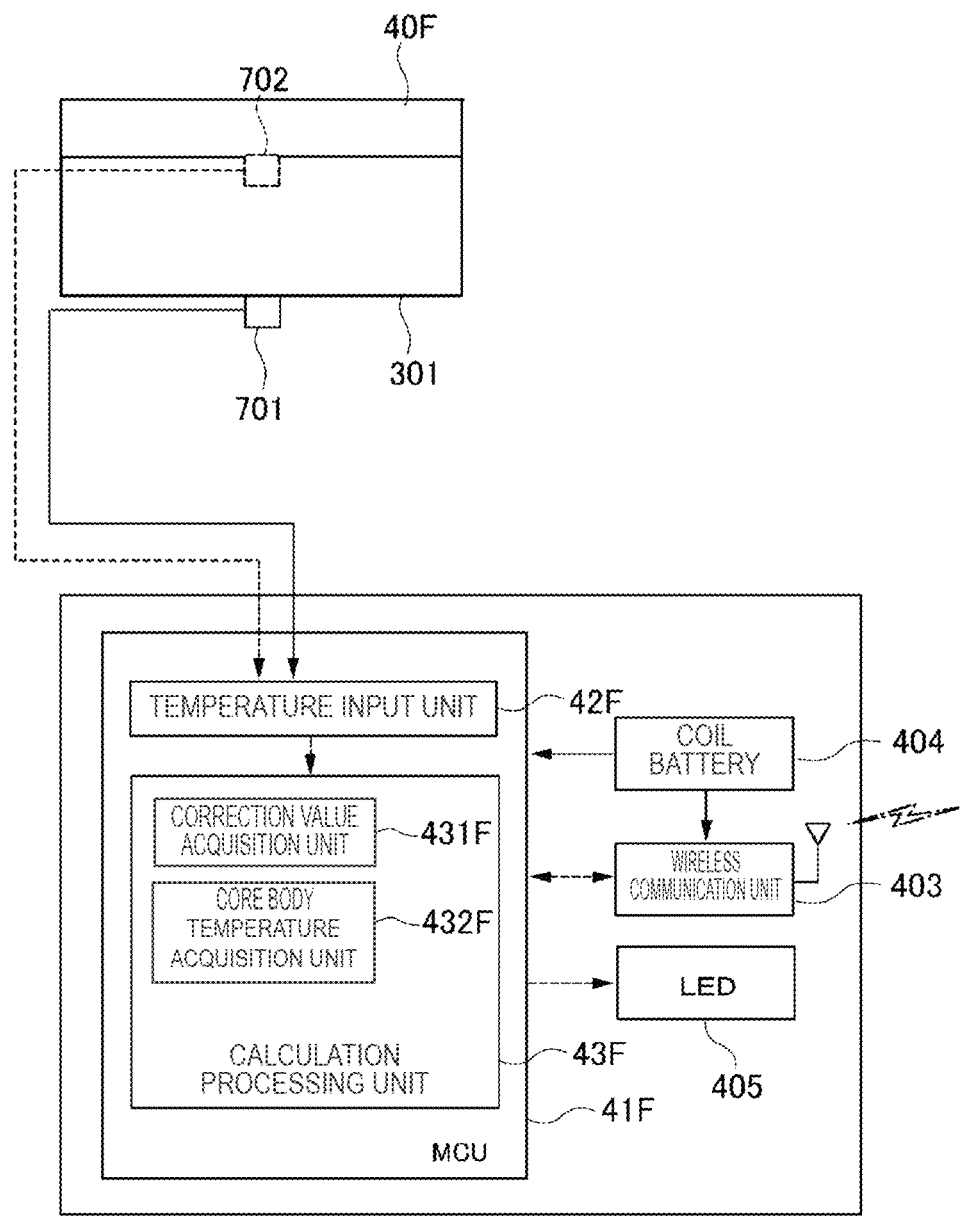
FIG. 12 is a block diagram showing the functional configuration of a processing unit that is a component of a sticking-type core body thermometer according to a second embodiment.

Next, a core body thermometer 1F according to a second embodiment will be described with reference to FIG. 12. Here, the description of components identical or similar to those of the above-described first embodiment is simplified or omitted, and differences will be mainly described. FIG. 12 is a block diagram showing the functional configuration of a processing unit 41F that is a component of the sticking-type core body thermometer 1F according to the second embodiment. Like reference signs denote identical or similar components to those of the first embodiment in FIG. 12.

The core body thermometer 1F acquires a core body temperature from only the first temperature (T1). Therefore, the core body thermometer 1F differs from the above-described core body thermometer 1 in that the core body thermometer 1F includes the processing unit 41F instead of the processing unit 41. The processing unit 41F differs from the above-described processing unit 41 in that the processing unit 41F includes a correction value acquisition unit 431F and a core body temperature acquisition unit 432F instead of the correction value acquisition unit 431 and the core body temperature acquisition unit 432. The other configuration is identical or similar to that of the core body thermometer 1, so the detailed description is omitted here.

The correction value acquisition unit 431F obtains a first correction value that is a correction value used to correct the first temperature, in accordance with a first differential value (subtracted value) that is a differential value between the first temperature (T1) and a reference temperature (T0) set in advance according to a limit body temperature up to which the body temperature feedback mechanism of the body works (for example, a maximum body temperature that a thermometer can take).

The correction value acquisition unit 431F sets a first correction value such that, in a range in which the first differential value (T0−T1) is greater than or equal to zero, the first correction value increases as the first differential value (T0−T1) increases and a rate of increase (slope) in the first correction value increases as the first differential value (T0−T1) increases. The methods of setting the reference temperature (T0) are as described above, so the detailed description is omitted here.

At this time, the correction value acquisition unit 431F, for example, obtains a first correction value from the first differential value (T0−T1) with a first function f that defines the relationship between first differential value (T0−T1) and first correction value. As described above, the first function f is a function of which, in the range in which the first differential value (T0−T1) is greater than or equal to zero, a first derivative f' is greater than or equal to zero and a second derivative f" is greater than or equal to zero.

A map (look-up table) may be used instead of the function (arithmetic expression) f to acquire a correction value (a first correction value). In other words, a map that defines the relationship between first differential value (T0−T1) and first correction value (that is, a first correction value map in which an associated first correction value is given for each lattice point of the first differential value (T0−T1)) may be stored in advance in the EEPROM or the like (storage unit), and a first correction value may be obtained by looking up the first correction value map in accordance with the first differential value (T0−T1). The obtained first correction value is output to the core body temperature acquisition unit 432F.

The core body temperature acquisition unit 432F obtains (estimates) a core body temperature by correcting the first temperature (T1) by using the first correction value (f(T0−T1)). For example, the core body temperature acquisition unit 432F calculates a core body temperature in accordance with, for example, the following expression 9.

$$\text{Core body temperature} = \text{First temperature } (T1) + \text{First correction value } (f(T0-T1)) \quad (9)$$

Figure 14:
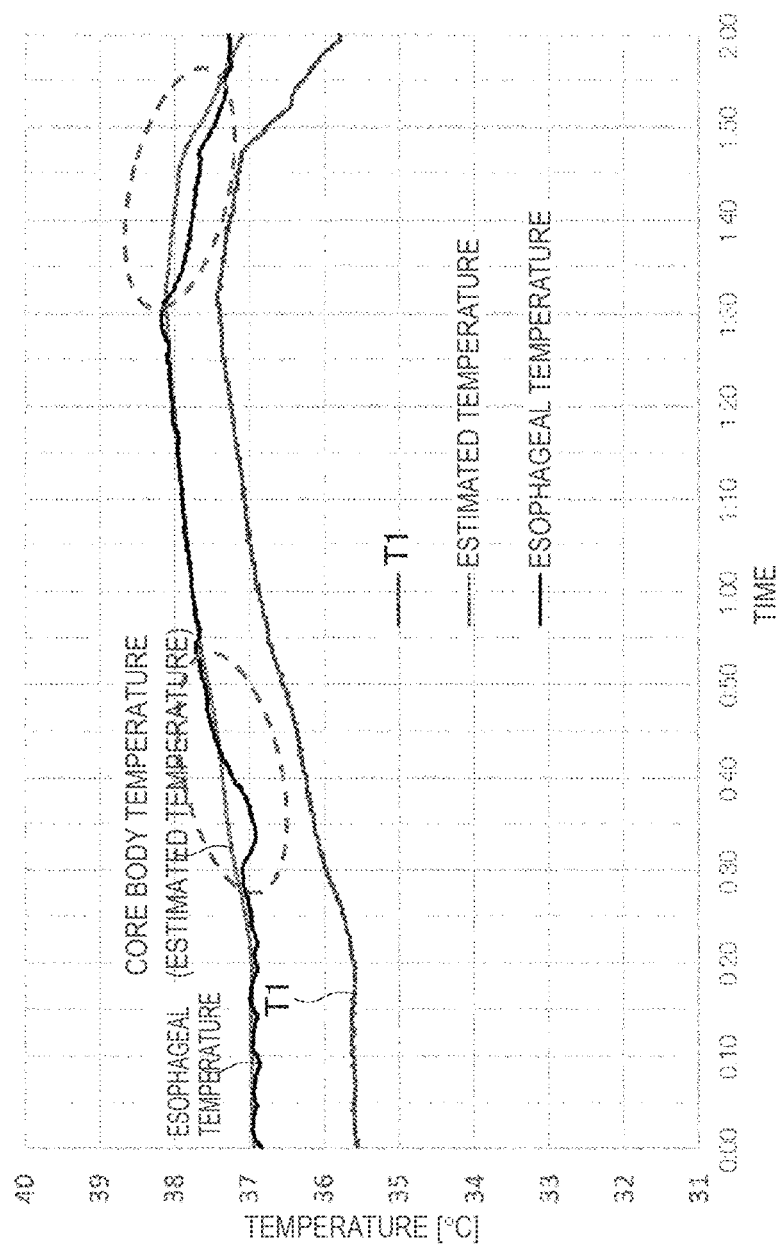
FIG. 14 is a graph showing an example of measurement results of first temperature (T1), core body temperature (estimated value), and esophageal temperature.

Here, an example of actually measured results is shown in FIG. 14. FIG. 14 is a graph showing an example of measurement results of first temperature (T1), core body temperature (estimated value), and esophageal temperature. In FIG. 14, the abscissa axis represents time, and the ordinate axis represents temperature (° C.). In the example of FIG. 14, the body temperature was increased by being placed under a high room temperature condition from a time point of 15 minutes to a time point of 1 hour 45 minutes and walking from a time point of 30 minutes to a time point of 1 hour 30 minutes, and the temperatures were measured. In other words, the core body thermometer IF was stuck to the body to make measurement, while a temperature sensor was inserted to esophagus through the nose to measure the esophageal temperature recognized as core body temperature. As shown in FIG. 14, even when the body temperature increases, the corrected core body temperature (estimated value) and the esophageal temperature substantially coincide with each other, so it is confirmed that correction is effectively functioning. In comparison with the measurement results shown in FIG. 13 (described above), although a deviation slightly increases in the area indicated by the dotted ellipse in the graph, it is confirmed that the corrected core body temperature (estimated value) and the esophageal temperature substantially coincide with each other.

Figure 15:
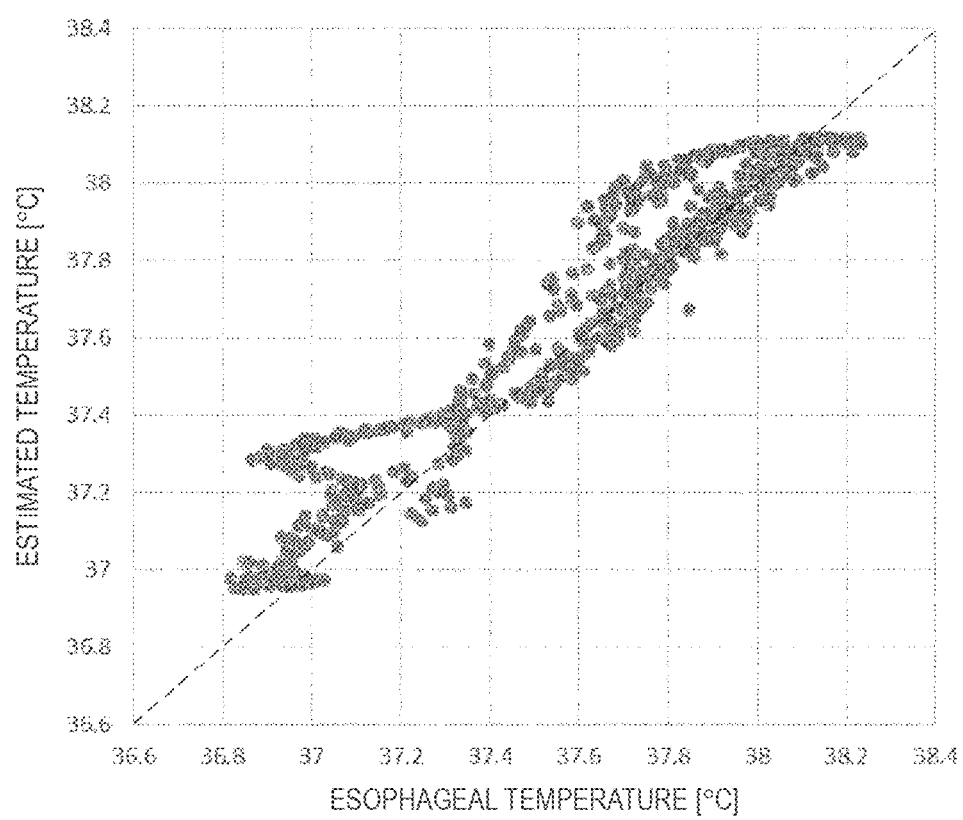
FIG. 15 is a graph showing an example of a relationship (correlation) between core body temperature (estimated value) and esophageal temperature.

FIG. 15 shows a graph in which corresponding points of the core body temperatures (estimated values) and the esophageal temperatures, shown in FIG. 14, are plotted. In FIG. 15, the abscissa axis represents esophageal temperature (° C.), and the ordinate axis represents core body temperature (estimated value) (° C.). As shown in FIG. 15, it is confirmed that the corrected core body temperature (estimated value) and the esophageal temperature have a good correlation.

According to the present embodiment, physiological response associated with thermoregulation by sweat and blood flow can be considered, so consistency with an actual core body temperature is enhanced. Thus, a core body temperature is highly accurately obtained with relatively simple calculation.

The embodiments of the present disclosure are described above; however, the present disclosure is not limited to the above-described embodiments and may be modified in various forms. For example, in the first embodiment and the first to third modifications of the first embodiment, the second thermal resistor 302, the third temperature sensor 703, and the fourth temperature sensor 704 may be omitted. In the second embodiment, the second thermal resistor 302, the first temperature sensor 701, the third temperature sensor 703, and the fourth temperature sensor 704 may be omitted.

Functions (arithmetic expressions) used for correction are not limited to those in the above-described embodiments or modifications, and other functions (arithmetic expressions) may be used. For example, a cubic function, an exponential function, a sine function (0 to 45°), or the like may be used.

In the embodiments, processes such as acquisition of correction values and calculation of core body temperatures are performed in the internal processing unit 41 (calculation processing unit 43). Alternatively, acquired temperature data may be transmitted wirelessly to, for example, an external server or mobile device (such as a smartphone), and calculations such as acquisition of correction values and calculation of core body temperatures may be performed in the server or the mobile device. In such a case, data such as the above-described functions, look-up tables, and the like are stored in memory of the server or mobile device as a library for calculation.

REFERENCE SIGNS LIST 1 core or deep body thermometer
10 upper exterior body
15 body temperature measurement unit
20 lower exterior body
30 thermal resistor layer
301 first thermal resistor
302 second thermal resistor
301a, 302a through-hole
40, 40F wiring substrate
41, 41B, 41C, 41D, 41E, 41F processing unit (processing circuit)
42, 42F temperature input unit (temperature input circuit)
43, 43B, 43C, 43D, 43E, 43F calculation processing unit (calculation processing circuit)
431, 431B, 431C, 431D, 431E, 431F correction value acquisition unit
432, 432B, 432C, 432D, 432E, 432F deep body temperature acquisition unit
403 wireless communication unit
407 FPC connector
50 flexible substrate
60 sticking member
601 first adhesion layer
602 second adhesion layer
603 vent layer
60a, 60b through-hole
701, 702, 703, 704 temperature sensor
80 lining member
80a through-hole
90 shock-absorbing member
90a through-hole

The invention claimed is:

1. A sticking-type core body thermometer configured to stick to a living body to measure a core body temperature, the sticking-type core body thermometer comprising:
    a thermal resistor having a predetermined thermal resistance;
    a first temperature sensor that is disposed on a first surface side of the thermal resistor and that detects a first temperature of a sticking surface side;
    a correction value acquisition unit that obtains a first correction value that is used to correct the detected first temperature based on a first differential value between (1) the detected first temperature and (2) a reference temperature set to a temperature higher than the first temperature,
    wherein the correction value acquisition unit sets the first correction value such that, in a range in which the first differential value is greater than or equal to zero, the first correction value increases as the first differential value increases and a rate of increase in the first correction value increases as the first differential value increases;
    a core body temperature acquisition unit that obtains a core body temperature by correcting the first temperature based on the first correction value; and
    a sticking member that includes:
        a first adhesion layer stuck to a lower exterior body of the sticking-type core body thermometer;
        a second adhesion layer that comes in contact with a subject, and
        a vent layer between the first adhesion layer and the second adhesion layer.

2. The sticking-type core body thermometer according to claim 1, wherein the reference temperature is set in advance according to a limit body temperature up to which a body temperature feedback mechanism of a body works.

3. The sticking-type core body thermometer according to claim 1, wherein the correction value acquisition unit obtains the first correction value from the first differential value with a first function that defines a relationship between the first differential value and the first correction value, and
    in a range in which the first differential value is greater than or equal to zero, a first derivative of the first function is greater than or equal to zero and a second derivative of the first function is greater than or equal to zero.

4. The sticking-type core body thermometer according to claim 1, further comprising:
    a second temperature sensor that is disposed on a second surface side of the thermal resistor and that detects a second temperature on a back surface side,
    wherein the correction value acquisition unit further obtains a second correction value used to correct the detected first temperature based on a second differential value that is between the detected first temperature and the detected second temperature, and the core body temperature acquisition unit obtains a core body temperature by correcting the detected first temperature by using the first correction value and the second correction value.

5. The sticking-type core body thermometer according to claim 1, further comprising a second temperature sensor that is disposed on a second surface side of the thermal resistor and that detects a second temperature on a back surface side,
    wherein the correction value acquisition unit further obtains a fifth correction value used to correct the detected first temperature, in accordance with a third differential value that is between the reference temperature and the detected second temperature, and
    the core body temperature acquisition unit obtains a core body temperature by correcting the detected first temperature by using the first correction value and the fifth correction value.

6. The sticking-type core body thermometer according to claim 5, wherein the correction value acquisition unit sets the fifth correction value such that, in a range in which the third differential value is greater than or equal to zero, the fifth correction value increases as the third differential value increases and a rate of increase in the fifth correction value decreases as the third differential value increases.

7. The sticking-type core body thermometer according to claim 5, wherein
    the correction value acquisition unit obtains the fifth correction value from the third differential value with a fifth function that defines a relationship between the third differential value and the fifth correction value, and
    in a range in which the third differential value is greater than or equal to zero, a first derivative of the fifth function is greater than or equal to zero and a second derivative of the fifth function is less than or equal to zero.

8. The sticking-type core body thermometer according to claim 5, wherein
    the correction value acquisition unit further obtains a sixth correction value used to correct the first differential value, in accordance with a time change in the first temperature, obtains a seventh correction value used to correct the first temperature, in accordance with a corrected first differential value corrected by using the sixth correction value, further obtains an eighth correction value used to correct the third differential value, in accordance with a time change in the second temperature, and obtains a ninth correction value used to correct the first temperature, in accordance with a corrected third differential value corrected by using the eighth correction value, and the core body temperature acquisition unit obtains a core body temperature by correcting the detected first temperature by using the seventh correction value and the ninth correction value.

9. The sticking-type core body thermometer according to claim 8, wherein the correction value acquisition unit sets the sixth correction value such that the sixth correction value increases as an amount of increase per unit time in the first temperature increases, and sets the seventh correction value such that the seventh correction value increases as a corrected first differential value corrected by using the sixth correction value increases and a rate of increase in the seventh correction value increases as a corrected first differential value corrected by using the sixth correction value increases, and the correction value acquisition unit sets the eighth correction value such that the eighth correction value increases as an amount of increase per unit time in the detected second temperature increases, and sets the ninth correction value such that the ninth correction value increases as a corrected third differential value corrected by using the eighth correction value increases and a rate of increase in the ninth correction value decreases as a corrected third differential value corrected by using the eighth correction value increases.

10. The sticking-type core body thermometer according to claim 8, wherein the correction value acquisition unit obtains the sixth correction value from a time change in the detected first temperature with a sixth function that defines a relationship between a time change in the detected first temperature and the sixth correction value, and obtains the seventh correction value from a corrected first differential value corrected by using the sixth correction value with a seventh function that defines a relationship between the seventh correction value and a corrected first differential value corrected by using the sixth correction value, the correction value acquisition unit obtains the eighth correction value from a time change in the detected second temperature with an eighth function that defines a relationship between a time change in the second temperature and the eighth correction value, and obtains the ninth correction value from a corrected third differential value corrected by using the eighth correction value with a ninth function that defines a relationship between the ninth correction value and a corrected third differential value corrected by using the eighth correction value, the sixth function monotonously increases with an increase in an amount of increase per unit time in the detected first temperature, and the eighth function monotonously increases with an increase in an amount of increase per unit time in the detected second temperature.

11. The sticking-type core body thermometer according to claim 4, further comprising:

two sensing units that each including the thermal resistor, the first temperature sensor, and the second temperature sensor, wherein the thermal resistors of the respective sensing units have different thermal resistance values, wherein the correction value acquisition unit obtains the correction value for each of the two sensing units, and wherein the core body temperature acquisition unit obtains two temporary core body temperatures by using the associated correction values for the respective two sensing units, obtains a core body temperature based on the two temporary core body temperatures, and obtains a likelihood of the core body temperature.

12. The sticking-type core body thermometer according to claim 1, wherein the vent layer comprises at least one of a nonwoven fabric, paper, wood, sponge and an open cell foamed material.

13. The sticking-type core body thermometer according to claim 1, wherein the vent layer comprises air inside.

14. A sticking-type core body thermometer configured to stick to a living body to measure a core body temperature, the sticking-type core body thermometer comprising:

a thermal resistor having a predetermined thermal resistance;

a first temperature sensor that is disposed on a first surface side of the thermal resistor and that detects a first temperature of a sticking surface side;

a correction value acquisition unit that obtains a first correction value that is used to correct the detected first temperature based on a first differential value between (1) the detected first temperature and (2) a reference temperature set to a temperature higher than the first temperature;

a second temperature sensor that is disposed on a second surface side of the thermal resistor and that detects a second temperature on a back surface side, wherein the correction value acquisition unit further obtains a second correction value used to correct the detected first temperature based on a second differential value that is between the detected first temperature and the detected second temperature, and the core body temperature acquisition unit obtains a core body temperature by correcting the detected first temperature by using the first correction value and the second correction value, wherein the correction value acquisition unit sets the second correction value such that, in a range in which the second differential value is greater than or equal to zero, the second correction value increases as the second differential value increases and a rate of increase in the second correction value decreases as the second differential value increases; and a sticking member that includes:
a first adhesion layer stuck to a lower exterior body of the sticking-type core body thermometer;
a second adhesion layer that comes in contact with a subject, and
a vent layer between the first adhesion layer and the second adhesion layer.

15. The sticking-type core body thermometer according to claim 14, wherein the correction value acquisition unit obtains the second correction value from the second differential value with a second function that defines a relationship between the second differential value and the second correction value, and in a range in which the second differential value is greater than or equal to zero, a first derivative of the second function is greater than or equal to zero and a second derivative of the second function is less than or equal to zero.

16. A sticking-type core body thermometer configured to stick to a living body to measure a core body temperature, the sticking-type core body thermometer comprising:
a thermal resistor having a predetermined thermal resistance;
a first temperature sensor that is disposed on a first surface side of the thermal resistor and that detects a first temperature of a sticking surface side;
a correction value acquisition unit that obtains a first correction value that is used to correct the detected first temperature based on a first differential value between (1) the detected first temperature and (2) a reference temperature set to a temperature higher than the first temperature;
a second temperature sensor that is disposed on a second surface side of the thermal resistor and that detects a second temperature on a back surface side,
wherein the correction value acquisition unit further obtains a second correction value used to correct the detected first temperature based on a second differential value that is between the detected first temperature and the detected second temperature, and the core body temperature acquisition unit obtains a core body temperature by correcting the detected first temperature by using the first correction value and the second correction value,
the correction value acquisition unit further obtains a third correction value used to correct the second differential value, in accordance with a time change in the detected first temperature, and obtains a fourth correction value used to correct the detected first temperature, in accordance with a corrected second differential value corrected by using the third correction value, and
the core body temperature acquisition unit obtains a core body temperature by correcting the detected first temperature by using the first correction value and the fourth correction value; and
a sticking member that includes:
a first adhesion layer stuck to a lower exterior body of the sticking-type core body thermometer;
a second adhesion layer that comes in contact with a subject, and
a vent layer between the first adhesion layer and the second adhesion layer.

17. The sticking-type core body thermometer according to claim 16, wherein the correction value acquisition unit sets the third correction value such that the third correction value increases as an amount of increase per unit time in the detected first temperature increases, and sets the fourth correction value such that the fourth correction value increases as a corrected second differential value corrected by using the third correction value increases and a rate of increase in the second correction value decreases as a corrected second differential value corrected by using the third correction value increases.

18. The sticking-type core body thermometer according to claim 16, wherein
the correction value acquisition unit obtains the third correction value from a time change in the detected first temperature with a third function that defines a relationship between a time change in the first temperature and the third correction value, and obtains the fourth correction value from a corrected second differential value with a fourth function that defines a relationship between the fourth correction value and a corrected second differential value corrected by using the third correction value,
the third function monotonously increases with an increase in an amount of increase per unit time in the detected first temperature, and
in a range in which the corrected second differential value is greater than or equal to zero, a first derivative of the fourth function is greater than or equal to zero and a second derivative of the fourth function is less than or equal to zero.

* * * * *